(12) United States Patent
Sengun et al.

(10) Patent No.: US 10,849,931 B2
(45) Date of Patent: Dec. 1, 2020

(54) COMPOSITIONS AND METHODS FOR PLATELET ENRICHED FIBRIN CONSTRUCTS

(75) Inventors: Mehmet Z. Sengun, Canton, MA (US); William Parrish, Hudson, MA (US); Gregory R. Whittaker, Stoneham, MA (US); Douglas A. Fifolt, Wrentham, MA (US); Brooks J. Story, Franklin, MA (US)

(73) Assignee: DEPUY SYNTHES PRODUCTS, INC, Raynham, MA (US)

( * ) Notice: Subject to any disclaimer, the term of this patent is extended or adjusted under 35 U.S.C. 154(b) by 395 days.

(21) Appl. No.: 13/250,086

(22) Filed: Sep. 30, 2011

(65) Prior Publication Data

US 2013/0084310 A1    Apr. 4, 2013

(51) Int. Cl.
| | |
|---|---|
| *A61K 35/14* | (2015.01) |
| *A61K 35/17* | (2015.01) |
| *A61K 38/18* | (2006.01) |
| *A61L 27/22* | (2006.01) |
| *A61L 27/38* | (2006.01) |
| *A61K 35/19* | (2015.01) |
| *A61L 27/54* | (2006.01) |

(Continued)

(52) U.S. Cl.
CPC ............. *A61K 35/17* (2013.01); *A61K 35/14* (2013.01); *A61K 35/19* (2013.01); *A61K 38/18* (2013.01); *A61K 38/1808* (2013.01); *A61K 38/1825* (2013.01); *A61K 38/1841* (2013.01); *A61K 38/1866* (2013.01); *A61K 38/1875* (2013.01); *A61K 38/363* (2013.01); *A61K 38/55* (2013.01); *A61L 15/32* (2013.01); *A61L 27/225* (2013.01); *A61L 27/38* (2013.01); *A61L 27/54* (2013.01); *A61L 2300/414* (2013.01)

(58) Field of Classification Search
None
See application file for complete search history.

(56) References Cited

U.S. PATENT DOCUMENTS 4,189,382 A * 2/1980 Zine, Jr. .................. 210/714
4,359,049 A 11/1982 Redl et al.
(Continued)

FOREIGN PATENT DOCUMENTS

EP         0 156 098 A2     10/1985
WO     WO 2010020254 A1 *  2/2010

OTHER PUBLICATIONS

David M. Dohan Ehrenfest, Lars Rasmusson and Tomas Albrektsson, Classification of platelet concentrates: from pure platelet-rich plasma (P-PRP) to leucocyte- and platelet-rich fibrin (L-PRF), 2009, Trends in Biotechnology vol. 27 No. 3, pp. 158-167.*

(Continued)

*Primary Examiner* — Renee Claytor
*Assistant Examiner* — Trent R Clarke

(57) ABSTRACT

Compositions and methods are provided for tissue constructs that promote wound healing. The composition comprises a dimensionally stable fibrin construct for local administration to a wound site or region. In one embodiment, the fibrin construct is a wound healing composition, including components that promote wound healing, such as platelets, growth factors, white blood cells and fibrin clots. In another embodiment, the tissue treatment composition includes (i) aggregated fibrin, (ii) blood cells, and (iii) optionally, growth factors and/or other proteins.

13 Claims, 27 Drawing Sheets

(51) Int. Cl.
*A61L 15/32* (2006.01)
*A61K 38/36* (2006.01)
*A61K 38/55* (2006.01)

(56) References Cited

U.S. PATENT DOCUMENTS

| | | | |
|---|---|---|---|
| 5,550,187 | A | 8/1996 | Rhee et al. |
| 5,733,545 | A * | 3/1998 | Hood, III .................. 424/93.72 |
| 5,744,545 | A | 4/1998 | Rhee et al. |
| 5,844,016 | A | 12/1998 | Sawhney et al. |
| 5,874,500 | A | 2/1999 | Rhee et al. |
| 6,730,299 | B1 | 5/2004 | Tayot et al. |
| 7,745,106 | B2 * | 6/2010 | Beretta et al. .................... 435/2 |
| 2003/0202970 | A1 * | 10/2003 | Liu et al. .................... 424/94.64 |
| 2004/0120942 | A1 * | 6/2004 | McGinnis et al. ......... 424/94.64 |
| 2010/0086529 | A1 * | 4/2010 | Mohammad et al. ..... 424/93.73 |

OTHER PUBLICATIONS

Robert a. S. Ariëns, Thung-Shenq Lai, John W. Weisel, Charles S. Greenberg and Peter J. Grant, Role of factor XIII in fibrin clot formation and effects of genetic polymorphisms, Blood, 2002 100: 743-754.*
E. Lucarelli, R. Beretta, B. Dozza, P.L. Tazzari, S.M. O'Connell, F. Ricci, M. Pierini, S. Squarzoni, P.P. Pagliaro, E.I. Oprita, and D. Donati, A Recently Developed Bifacial Platelet-Rich Fibrin Matrix, published Jul. 1, 2010, European Cells and Materials, vol. 20, pp. 13-23.*
Document "ASTM D882" retrieved from the American Society for Testing and Materials webpage at http://www.astm.org/Standards/D882.htm on Oct. 30, 2012.*
David M. Dohan, Joseph Choukroun, Antoine Diss, Steve L. Dohan, Anthony J. J. Dohan, Jaafar Mouhyi, and Bruno Gogly, Platelet-rich fibrin (PRF): A second-generation platelet concentrate. Part I: Technological concepts and evolution, 2006, Oral Surg Oral Med Oral Pathol Oral Radiol Endod 101:E37-44.*
Hed J, Johansson M, Lindroth M. Complement activation according to the alternate pathway by glass and plastic surfaces and its role in neutrophil adhesion. 1984, Immunology Letters 8(6):295-9. (Abstract only).*
Sophia Harrison, Patrick Vavken, Sherwin Kevy, May Jacobson, David Zurakowski, and Martha M. Murray, Platelet Activation by Collagen Provides Sustained Release of Anabolic Cytokines, 2011, Am J Sports Med. 39(4): 729-734, published online Mar. 11, 2011.*
Sashwati Roy, Jason Driggs, Haytham Elgharably, Sabyasachi Biswas, Muna Findley, Savita Khanna, Urmila Gnyawali, Valerie K. Bergdall, Chandan K. Sen, Platelet-rich fibrin matrix improves wound angiogenesis via inducing endothelial cell proliferation, 2011, Wound Rep Reg, vol. 19, pp. 753-766, published online Nov. 1, 2011.*
Manabu Sato and Hiroaki Harasaki, Evaluation of Platelet and Coagulation Function in Different Animal Species Using the Xylum Clot Signature Analyzer, 2002, ASAIO Journal, vol. 48, pp. 360-364.*
Sommerey et al., Thromboelastography in healthy dairy cows, 2014, J. Dairy Sci., vol. 97, pp. 5474-5480.*
Scarpelini et al., Normal range values for thromboelastography in healthy adult volunteers, 2009, Braz. J. Med. Biol. Res., vol. 42, pp. 1210-1217.*
NPL document "Sorvall RC-3C brochure" available online at https://www.djblabcare.co.uk/djb/data/sheet/268029876/Sorvall_RC_3C-Brochure.pdf, accessed Mar. 28, 2017.*
NPL document "Thermo Scientific Rotor Guide" available online at https://tools.thermofisher.com/content/sfs/brochures/Large-Capacity-Centrifuge-Rotors-EN.pdf, accessed Apr. 2, 2017.*
Sabrina Meo, Ruggero Dittadi and Massimo Gion, Biological variation of vascular endothelial growth factor, 2005, Clin Chem Lab Med, vol. 43, No. 3, pp. 342-343.*
Yoka H. Kusumanto, Wendy A. Dam, Geke A.P. Hospers, Coby Meijer & Nanno H. Mulder, Platelets and granulocytes, in particular the neutrophils, form important compartments for circulating vascular endothelial growth factor, 2003, Angiogenesis, vol. 6, pp. 283-287.*
Petri Salven, Arto Orpana, and Heikki Joensuu, Leukocytes and Platelets of Patients with Cancer Contain High Levels of Vascular Endothelial Growth Factor, 1999, Clinical Cancer Research, vol. 5, pp. 487-491.*
K. Werther, I. J. Christensen & H. J. Nielsen, Determination of vascular endothelial growth factor (VEGF) in circulating blood: significance of VEGF in various leucocytes and platelets, 2002, Scandinavian Journal of Clinical and Laboratory Investigation, vol. 62, No. 5, pp. 343-350.*
RE Banks, MA Forbes, SE Kinsey, A Stanley, E Ingham, C Walters and PJ Selby, Release of the angiogenic cytokine vascular endothelial growth factor (VEGF) from platelets: significance for VEGF measurements and cancer biology, 1998, British Journal of Cancer, vol. 77, No. 6, pp. 956-964.*
Seok Jin Kim et al., Serum Vascular Endothelial Growth Factor per Platelet Count in Hepatocellular Carcinoma: Correlations with Clinical Parameters and Survival, 2004, Jpn J Clin Oncol, vol. 34, No. 4, pp. 184-190.*
Cliona C Kirwan, Gerard J Byrne, Shant Kumar and Garry McDowell, Platelet release of Vascular Endothelial Growth Factor (VEGF) in patients undergoing chemotherapy for breast cancer, 2009, Journal of Angiogenesis Research, vol. 1, Article 7, pp. 1-9.*
NPL document "Platelet count" is a screenprint of a webpage from MedicineNet showing the normal range of platelets per μl in whole blood, accessed at https://www.medicinenet.com/script/main/artasp?articlekey=9939 on Feb. 10, 2018.*
Blombäck et al., Fibrin in human plasma: Gel architectures governed by rate and nature of fibrinogen activation. Thrombosis Res. 1994;7(5):521-38.
Mosesson et al., The structure and biological features of fibrinogen and fibrin. Reprint from Fibrinogen. Ann N Y Acad Sci. 2001;936:11-30.
Craig et al., A Biological Comparison of Polyglactin 910 and Polyglycolic Acid Synthetic Absorbable Sutures. Surg. 1010, 1975.
Gilman et al., Pharmacological Basis of Therapeutics, 8th Ed. McGraw Hill Inc., NY. p. 1311-31. 1990.

* cited by examiner

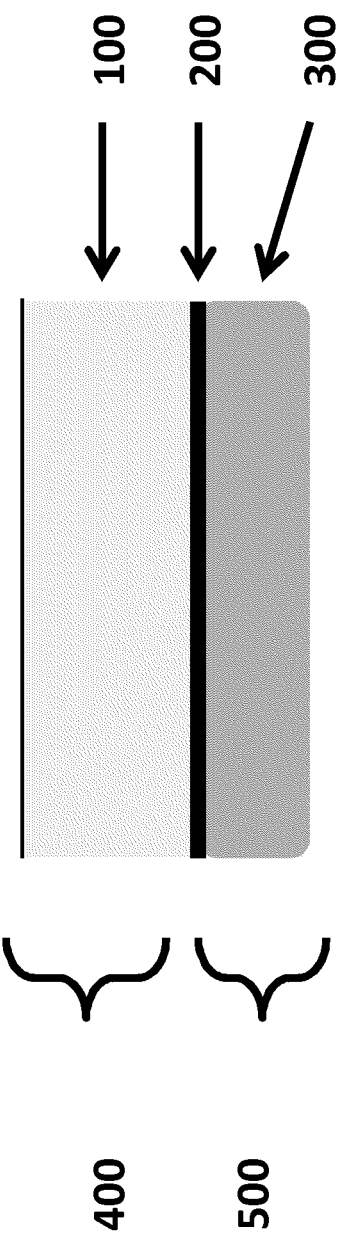

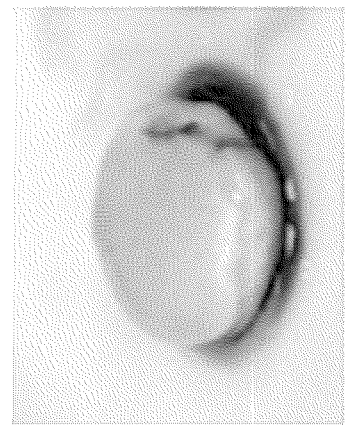
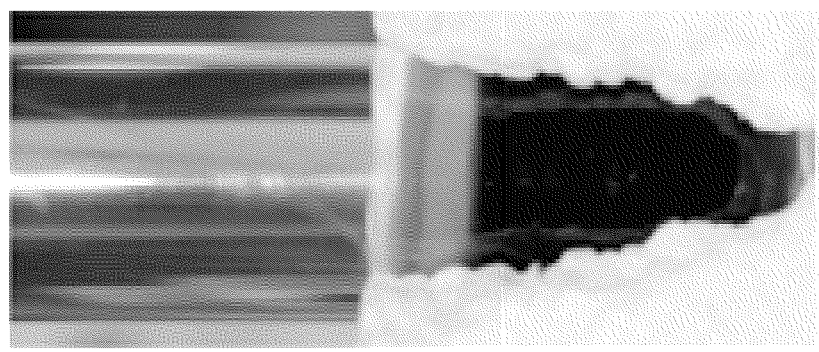
Figure 11

COMPOSITIONS AND METHODS FOR PLATELET ENRICHED FIBRIN CONSTRUCTS

FIELD OF THE INVENTION

The present invention relates generally to compositions and methods of platelet enriched fibrin constructs for delivery.

BACKGROUND OF THE INVENTION

Wound healing, or wound repair, is an intricate process in which the skin (or another organ-tissue) repairs itself after injury. In normal skin, the epidermis and dermis exists in a steady-state equilibrium, forming a protective barrier against the external environment. Once the protective barrier is broken, the normal (physiologic) process of wound healing is immediately set in motion. The classic model of wound healing is divided into three or four sequential, yet overlapping phases: (1) hemostasis, (2) inflammatory, (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active hemostasis.

Fibrin clots act as a hemostatic barrier to reduce the risk of serum, lymph and liquid leakage and are frequently used to reduce blood loss during/after surgery. The fibrin sealants, formed by mixing a concentrated solution of fibrinogen with thrombin and calcium ions to produce fibrin, are impractical because the preparation method requires several hours and results in a crude clotting factor concentrate that is useful to manage hemostatically-deficient patients, but is not practical for harvesting fibrinogen from small volumes of blood.

Fibrin glues are well-known in the art for use in hemostasis, tissue sealing and wound healing, and have been commercially available outside the United States for more than a decade. Fibrin glues mimic the last step of the coagulation cascade and are usually commercialized as kits comprising components to form a three-dimensional network commonly called "Fibrin Gel." However, an important and well known disadvantage of the known fibrin glue preparations resides in the water-like fluidity of the components, which leads to considerable handling difficulties of the glues. Efforts have been made to overcome this problem and facilitate the mixing of the components by the development of particular application modes such as a double-syringe applicator (e.g. that supplied under the trade name Duploject®, Immuno AG, Vienna, Austria, and which is disclosed in e.g. U.S. Pat. No. 4,359,049, or a special spray system as disclosed in e.g. EP-A-156 098). The basic problem with a low viscosity glue still remains.

Multiple problems exist with the present tissue sealants. First, a non-viscous or low viscosity glue is unsuitable for use on non-horizontal surfaces since it will run off before setting. Second, there is a definite risk of a non-viscous or low vicosity glue running off to sites where it is unwanted and where it might cause complications. This is particularly the case in vascular surgery since the fluid glue may reach inside the vessels before it sets and thereby cause thromboembolic complications. An instantaneously setting fibrin glue (containing a high concentration of thrombin), on the other hand, cannot be used where the parts to be sealed require subsequent adaptation.

Moreover, the present solutions do little to expedite wound healing. Recombinant or xenogenic growth factors can be targeted for delivery to a desired site within a subject to speed and the healing process. However, delivery vehicles for growth factors are not always reliable or able to remain in the desired location for a sufficient period of time. Moreover, formulation and delivery of multiple growth factors, which are often needed for improved healing, are not practical due to cost and availability.

Therefore, a need remains for improved methods and compositions for wound healing, and specifically for methods and compositions to deliver multiple growth factors to a site for tissue healing and/or repair.

SUMMARY OF THE INVENTION

The present invention generally provides compositions and methods for preparing a wound healing construct. One aspect discloses a method of preparing a growth factor enriched construct including the steps of collecting a blood sample, mixing the blood sample in a container, exposing the blood mixture to a separation force and harvesting a dimensionally stable, suturable fibrin construct. Another aspect discloses a bioimplantable construct including a fibrin construct having a growth factor enriched surface and a growth factor depleted surface, where the fibrin construct is dimensionally stable and suturable. An additional aspect discloses method of regenerating, repairing or augmenting damaged or injured tissue in a subject by obtaining a fibrin construct and delivering the fibrin construct to a target site. Yet another aspect discloses a kit including a borosilicate container, an anti-coagulant, a coagulation activator, and a cross-linking agent.

One aspect includes a method of preparing a growth factor enriched construct by collecting a blood sample comprising unaggregated fibrin in the presence of an anti-coagulant, mixing the blood sample in a container with a coagulation activator to initiate aggregation of the fibrin, exposing the blood mixture to a separation force that separates the blood mixture into a gradient of plasma, aggregated fibrin and blood cells, and harvesting the aggregated fibrin and at least a portion of the blood cells to form a dimensionally stable, suturable fibrin construct, wherein the fibrin construct has a growth factor enriched surface concentrated with white blood cells and platelets capable of releasing a growth factor and an opposed, growth factor depleted surface. The growth factor depleted surface can be substantially lacking in blood cells. The growth factor depleted surface can be substantially lacking in red blood cells.

In one embodiment, the method includes the fibrin construct having particular physical properties to be dimensionally stable. The physical properties can include durability under stress and resiliency. In an exemplary embodiment, the fibrin construct can have a resiliency that is measured by an elongation at break strength of at least 200%. In another exemplary embodiment, the fibrin construct can have a strength that is measured by an ultimate strength of at least 0.15 MPa. In yet another exemplary embodiment, the fibrin construct can have a strength that is measured by a compression strength of at least 30 kPa.

In another embodiment, the method can include the fibrin construct having blood cells, such as can include platelets, white blood cells, and/or red blood cells, where the platelets can further include unactivated and activated platelets. In an exemplary embodiment, the blood cells include white blood cells and platelets.

In yet another embodiment, the method can include obtaining the blood sample from a single donor or from multiple donors mixed together to obtain a single blood sample. The blood sample can further be obtained from the same subject who will receive the fibrin construct. Thus, the blood is autologous to the recipient. The blood sample can also be obtained from a non-autologous subject or donor or multiple donors. Moreover, the blood sample can be obtained from a heterologous subject or donor or multiple donors. Thus, the blood sample can be obtained from one or more subjects. In an exemplary embodiment, the blood sample can be obtained from a single donor or from multiple donors.

In one more embodiment, the method can include mixing the blood sample in a container, such as glass. The container can be a borosilicate glass container.

The blood sample can also be mixed with one or more coagulation activators or clotting factors to induce coagulation. In a particular embodiment, the coagulation activator can be calcium chloride.

The blood sample can also be exposed to one or more separation forces, such as centrifugation. In an exemplary embodiment, the separation force includes more than one centrifugations. The first centrifugation can be at a speed of at least 2000×g and an optional second centrifugation can be at a speed of at least 2000×g. In an additional embodiment, the separation force includes a single centrifugation at a force of at least 2000×g, but preferably at least 3000×g.

The method can also include modifying the fibrin construct after harvest. Such modifications can include removing excess liquid from the fibrin construct by blotting the fibrin construct on an absorbent material; folding the fibrin construct upon itself to form a folded construct such that adjacent halves of the growth factor enriched surface contact each other and form an inner portion of the folded construct while growth factor depleted surface forms an outer portion of the folded construct; forming a multilayered construct by layering a second fibrin construct on top of the first fibrin construct such that the growth factor enriched surfaces of each construct are in contact with each other and the growth factor depleted surfaces of each of the constructs form outer surfaces of the multilayered construct; and cross-linking the fibrin construct.

Another aspect discloses an bioimplantable construct including a fibrin construct derived from whole blood, having a growth factor enriched surface concentrated with blood cells and platelets capable of releasing a growth factor and a growth factor depleted surface, the fibrin construct being dimensionally stable and suturable. The growth factor depleted surface can also be substantially lacking in blood cells, such as red blood cells, white blood cells, platelets. The growth factor depleted surface can be substantially lacking in red blood cells. In another embodiment, the growth factor depleted surface can include white blood cells.

The fibrin construct can have particular physical properties that further define its dimensional stability. The physical properties can include durability under stress and resiliency. In an exemplary embodiment, the fibrin construct can have a resiliency that is measured by an elongation at break strength of at least about 200%. In another exemplary embodiment, the fibrin construct can have a strength that is measured by an ultimate strength of at least about 0.15 MPa. In yet another exemplary embodiment, the fibrin construct can have a strength that is measured by a compression strength of at least about 30 kPa.

The fibrin construct can also be modified. Such modifications can protect one or more sides of the fibrin construct. In an exemplary embodiment, the fibrin construct is a folded construct that is folded upon itself so that adjacent halves of the growth factor enriched layer contact each other and form an inner portion of the folded construct while the growth factor depleted surface forms an outer portion of the folded construct. The fibrin construct can further be sutured along at least one edge thereof to secure the folded construct in the folded condition.

The fibrin construct can also be in the form of a multilayered construct in which two fibrin constructs are joined together with the growth factor enriched surfaces facing each other forming an inner portion of the multilayered construct and the growth factor depleted surfaces forming an outer portion of the multilayered construct. Like the folded construct, the multilayered construct can also include sutures extending between the adjacent constructs along at least a portion of an edge thereof to secure the multilayered construct An additional aspect includes a method of regenerating, repairing or augmenting damaged or injured tissue in a subject by obtaining a fibrin construct as disclosed and delivering the fibrin construct to a target site in the subject to regenerate, repair or augment damaged or injured tissue.

In one embodiment, the method can include obtaining the blood sample from a single donor or from multiple donors mixed together to obtain a single blood sample. The blood sample can further be obtained from the same subject who will receive the fibrin construct. Thus, the blood is autologous to the recipient. The blood sample can also be obtained from a non-autologous subject or donor or multiple donors. Moreover, the blood sample can be obtained from a heterologous subject or donor or multiple donors. Thus, the blood sample can be obtained from one or more subjects. In an exemplary embodiment, the blood sample can be obtained from a single donor or from multiple donors.

In another embodiment, the method can include delivering the one or multiple fibrin constructs to a target site. Multiple fibrin constructs can be joined together prior to delivery to the target site, such as by suturing and/or gluing the fibrin constructs together. One or more fibrin constructs can also be shaped to correspond to the target site. Shaping the fibrin constructs can include joining multiple fibrin constructs, such as by suturing and gluing the fibrin constructs together, prior to delivery. In an exemplary embodiment, the fibrin constructs can be shaped to correspond to the target site by stretching, suturing, compressing, trimming and blotting one or more fibrin constructs.

In another embodiment, the method can include delivering the fibrin construct with optional components that can be added either during or after preparing the fibrin construct. The optional components can include at least one growth factor. The growth factor can be any that are elaborated from platelets including vascular endothelial growth factor (VEGF), epidermal growth factor (EGF), heparin-binding epidermal-like growth factor (HBGF), insulin-like growth factor (IGF), platelet-derived growth factor (PDGF-$\alpha\beta$), transforming growth factor (TGF-$\beta$), bone morphogenic protein (BMP), and fibroblast growth factor (FGF). The optional component can also include an agent, such as a fibrinolysis inhibitor, a plasmin inhibitor, aprotinin, aprilotinin, alpha-2-antiplasmin, alpha-2-macroglobulin, alpha-1-antitrypsin, epsilon-aminocaproic acid or tranexamic acid, and a plasmin activator inhibitor.

Yet another aspect discloses a kit including a borosilicate container for receiving a whole blood sample. The kit can include an anti-coagulant, and a coagulation activator.

The kit can also include a blood collection apparatus, such as a syringe, for receiving a whole blood sample. The syringe can also be adaptable to or removable from the container to collect the blood directly into the container. In one particular embodiment, the anti-coagulant is ACD-A (anticoagulant citrate dextrose solution A).

The anti-coagulant of the kit can include, but is not limited to, heparin, EDTA, citrate, oxalate, thrombin inhibitors, or other factor inhibitors. The anti-coagulant can be in powder, liquid or lyophilized form. The anti-coagulant can also be included at a concentration and/amount appropriate for the volume of blood to be collected or the volume blood that can be added to the container.

The kit can also include a coagulation activator, such as an ionic coagulation activator. The coagulation activator can include, but is not limited to, zeolites, hemostatic agents, calcium ions, calcium salts, Factor I, Factor II, Factor III, Factor IV, Factor V, Factor VII, Factor X, Factor XI, Factor XII, Factor XIII, thrombokinase, proaccelerin, proconvertin, antihemophilic globulin, Christmas factor, prothombinase, plasma thromboplastin antecedent, Hageman factor, adenosine diphosphate, collagen, arachidonic acid, and fibinase. In an exemplary embodiment, the coagulation activator can be calcium chloride.

The kit can further include a cross-linking agent. The cross-linking agent can include nonlimiting examples, such as a condensing agent, a photosensitive material, an aldehyde, such as glutaraldehyde, and carbodiimide EDC (1-ethyl-3(3 dimethyl aminopropyl)).

BRIEF DESCRIPTION OF THE DRAWINGS

The appended drawings have been included herein so that the above-recited features, advantages and objects will become clear and can be understood in detail. These drawings form a part of the specification. It is to be noted, however, that the appended drawings illustrate exemplary embodiments and should not be considered to limit the scope.

FIG. 3 is a schematic diagram of the fibrin construct showing the growth factor depleted and growth factor enriched surfaces;

FIG. 11 shows the hard spin (~3000×g) method of preparing the PEFC;

DETAILED DESCRIPTION OF THE INVENTION

Figure 1:
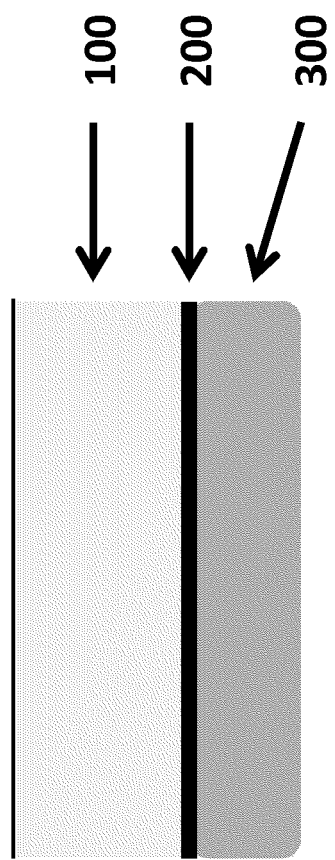
FIG. 1 is a schematic diagram of the fibrin construct with the fibrin layer platelet/WBC/growth factor layer and the RBC layer.

Certain exemplary embodiments will now be described to provide an overall understanding of the principles of the structure, function, manufacture, and use of the constructs and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Blood clotting assists homeostasis by minimizing blood loss. Generally, blood clotting requires vessel damage, platelet aggregation, coagulation factors and inhibition of fibrinolysis. The coagulation factors act through a cascade that relates the vessel damage to formation of a blood clot (see generally L. Stryer, Biochemistry, 3rd Ed, W.H. Freeman Co., New York; and A. G. Gilman et al., The Pharmacological Basis of Therapeutics, 8th Edition, McGraw Hill Inc., New York, pp. 1311-1331).

Blood is made up of liquid and solid components. Blood plasma is the liquid component of blood, in which the blood cells (solid component) are suspended. It makes up about 60% of total blood volume. It is composed of mostly water (90% by volume), and contains dissolved proteins, glucose, clotting factors, mineral ions, hormones and carbon dioxide.

Platelets are blood cells found in the solid component of whole blood. Platelets and blood proteins work together to stop the bleeding by initiating blood clotting, or coagulation, and forming a clot over the injury. Platelets exert strong procoagulant and antifibrinolytic effects through the release of many growth factors, such as transforming growth factor (TGF-β1), platelet-derived growth factor (PDGF-αβ), and vascular endothelial growth factor (VEGF).

One prevalent blood protein is fibrinogen (Factor I). As used herein the terms "unaggregated fibrin" and "fibrinogen" are used interchangeably to refer to a precursor to fibrin or in its state prior to clotting or coagulation. Fibrinogen is a 340 KDa glycoprotein hexamer containing two sets of three different chains (α, β, and γ), linked to each other by disulfide bonds that is synthesized by the liver. In a healthy individual, fibrinogen or unaggregated fibrin has two principle functions, 1) to form bridges for platelets by binding to their surface proteins and 2) a precursor to fibrin.

Coagulation begins almost instantly after an injury to the blood vessel has damaged the endothelium. During the clotting process, fibrinogen is converted to fibrin through several steps. First, thrombin cleaves the amino-terminus of the fibrinogen alpha and beta chains to fibrinopeptide A and B, respectively. The resulting fibrin monomers polymerize end to end to form protofibrils, which in turn associate laterally to form fibrin fibers. The fibrin fibers are then capable of associating to form the fibrin gel or clot. As used herein the terms "aggregated fibrin," "fibrin," and "polymerized fibrin" are used interchangeably to refer to fibrin in its state after clotting or coagulation. Fibrin can also be cross linked, such as by Factor XIII, to add strength to the clot.

Due to its adhesive properties, a fibrin clot atraumatically connects tissues by forming a strong joint between the tissues and adapts uneven wound surfaces. The fibrin clot promotes the ingrowth of fibroblasts which, in combination with efficient hemostasis and adhesion between the wound surfaces, provides for an improved healing process.

It has been discovered that dimensionally stable, fibrin constructs can be reproducibly obtained from clotted blood and can substantially promote wound healing. For example, fibrin constructs are useful for local administration to a wound site or region. The fibrin constructs can also include components that promote wound healing, such as platelets, growth factors, white blood cells, aggregated fibrin and growth factors and/or other proteins.

The Fibrin Construct

Figure 2:
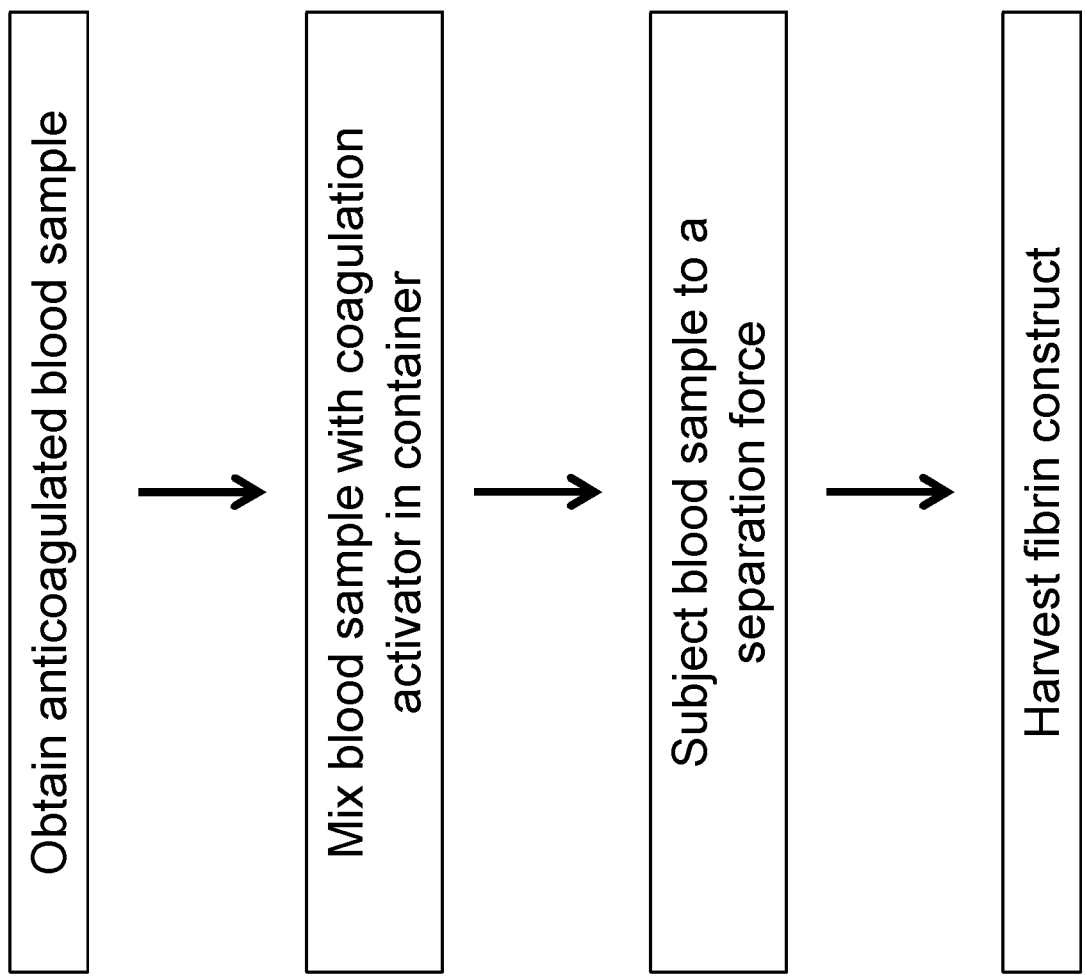
FIG. 2 shows one embodiment of the method of preparing the fibrin construct.

The fibrin construct described herein can include a fibrin layer 100 a platelet/white blood cell/growth factor layer 200 and a red blood cell layer 300 as shown FIG. 1. The fibrin construct can be obtained by a method of clotting or coagulating blood in a container and separating the fibrin construct from unwanted components of the blood. In one embodiment, a method of preparing the fibrin construct can include the steps of obtaining a blood sample from a subject, mixing the blood sample with a calcium ion in a container, exposing the blood sample to a separation force and harvesting the fibrin construct. FIG. 2 is a flow chart illustrating the steps of such a method.

The terms "clot," "clotting," "coagulation," are used interchangeably herein, refer to a soft, nonrigid insoluble mass formed when blood gels or the process of forming the soft, nonrigid insoluble blood mass. The term "clot" can apply to the coagulated phase of blood; the soft, coherent, jelly-like mass resulting from the conversion of fibrinogen to fibrin, thereby entrapping blood cells (and offer formed elements) within the coagulated plasma.

The fibrin construct described herein can be derived from coagulated blood. In one embodiment, the fibrin construct is obtained from a sample of blood, whole blood, or a sample of a blood derivative such as blood containing an additive or diluent, or a derivative of blood, such as plasma; white blood cells; red blood cells; platelets; plasma and white blood cells; plasma and platelets; plasma, red blood cells and platelets; plasma, white blood cells and platelets; or any combination thereof.

The blood sample can be obtained from a single donor or from multiple donors and mixed together to obtain a single blood sample. The blood sample can further be obtained from the same subject who will receive the fibrin construct. Thus, the blood can be autologous to the recipient. The blood sample can also be obtained from a non-autologous subject or donor or multiple donors. Moreover, the blood sample can be obtained from a heterologous subject or donor or multiple donors. Thus, the blood sample can be obtained from one or more subjects.

The term "subject" as used herein refers to an animal, in one embodiment, a mammal and in another embodiment, a human, who can benefit from the compositions and methods of the present invention. There is no limitation on the type of animal that could benefit from the present methods. A subject regardless of whether a human or non-human animal may be referred to as an individual, subject, animal, host or recipient. The methods of the present invention have applications in human medicine, veterinary medicine as well as in general, domestic or wild animal husbandry. In one embodiment, the candidate subject is a mammal such as a human, laboratory test animal, such as a mouse, rat, rabbit, guinea pig, hamster or avian species, such as a poultry bird and veterinary medical animal, such as dog, cat, horse, cow, sheep, etc.

Moreover, the blood sample can be less than about 0.1 ml or about 0.1 ml, 0.2 ml, 0.3 ml, 0.4 ml, 0.5 ml, 0.6 ml, 0.7 ml, 0.8 ml, 0.9 ml, 1.0 ml, 1.5 ml, 2 ml, 2.5 ml, 3 ml, 3.5 ml, 4 ml, 4.5 ml, 5 ml, 5.5 ml, 6 ml, 6.5 ml, 7 ml, 7.5 ml, 8 ml, 8.5 ml, 9 ml, 9.5 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 35 ml, 40 ml, 45 ml, 50 ml, 55 ml, 60 ml, 65 ml, 70 ml, 75 ml, 80 ml, 85 ml, 90 ml, 95 ml, 100 ml, 110 ml, 120 ml, 130 ml, 140 ml, 150 ml, 160 ml, 170 ml, 180 ml, 190 ml, 200 ml, 225 ml, 250 ml, 275 ml, 300 ml, 325 ml, 350 ml, 375 ml, 400 ml, 425 ml, 450 ml, 475 ml, 500 ml, 550 ml, 600 ml, 650 ml, 700 ml, 800 ml, 900 ml, 1000 ml or more. In an exemplary embodiment, the blood sample can be in the range of about 0.5 ml to about 300 ml.

In another exemplary embodiment, the blood sample can be in the range of about 1 ml to about 100 ml. In yet another exemplary embodiment, blood sample can be in the range of about 5 ml to about 50 ml.

The blood sample can be exposed to an anti-coagulant during or after collection of the sample to permit ease of handling the blood. Anti-coagulants such as heparin, anti-coagulant citrate dextrose solution A (ACD-A), EDTA, citrate, oxalate, thrombin inhibitors, or other factor inhibitors can be used. The anti-coagulant can be added to the blood collection container prior to collection or directly after collection of the blood sample to prevent premature coagulation.

After obtaining the blood sample, the blood can be placed in a container. The container can be made of agents that do not substantially degrade within, permeate through, react with or otherwise experience deleterious effects as a result of storage; or, more particularly, as a result of a chemical interaction with the materials used with the container. Exemplary embodiments of containers can include various types of glass, such as borosilicate glass. Borosilicate glass is a type of glass having silica and boron oxide as the main glass-forming constituents. The boric oxide makes the glass resistant to extreme temperatures, and also improves its resistance to chemical corrosion. Therefore, borosilicate glasses are known for having very low coefficients of thermal expansion and high softening point, offering a high level of resistance to attack from water, acids, salt solutions, organic solvents and halogens.

After placing the blood sample in a container, the blood sample can be exposed to or mixed with one or more coagulation activators or clotting factors to induce coagulation. Examples of coagulation activators or clotting factors can include, but are not limited to, zeolites, hemostatic agents, calcium ions, calcium salts, bivalent calciums, thrombin, Factor I, Factor II, Factor III, Factor IV, Factor V, Factor VII, Factor X, Factor XI, Factor XII, Factor XIII, thrombokinase, proaccelerin, proconvertin, antihemophilic globulin, Christmas factor, prothombinase, plasma thromboplastin antecedent, Hageman factor, and fibinase. The coagulation activators or clotting factors can be added to the blood in an appropriate amount relative to the blood sample. For example, the concentration of calcium chloride can vary, e.g. between 10 mM to 0.5 M. In an exemplary embodiment, calcium salts, such as found in calcium chloride, can be added to the blood sample to form calcium ions and mixed with the blood to induce coagulation of the blood sample.

The blood sample can also be exposed to one or more separation forces. The separation force can include, but is not limited to, centrifugal forces such as centrifugation. The separation force can separate the blood components according to density and size. In one embodiment, the separation force separates the blood into a density gradient. In another embodiment, the separation force separates the blood into a gradient of plasma, fibrin and blood cells. In yet another embodiment, the separation force separates the blood into a gradient of plasma, aggregated fibrin and blood cells. The blood cells can include one or more of red blood cells, platelets, and white blood cells. Moreover, the centrifugation force can be a speed of at least about 200×g, 500×g, 1000×g, 1500×g, 1600×g, 1700×g, 1800×g, 1900×g, 2000×g, 2100×g, 2200×g, 2300×g, 2400×g, 2500×g, 2600×g, 2700×g, 2800×g, 2900×g, 3000×g or greater, or any speed in between. In an exemplary embodiment, centrifugation force can be a speed of at least about 1500×g. In another exemplary embodiment, centrifugation force can be a speed of at least about 2000×g. In yet another exemplary embodiment, centrifugation force can be a speed of at least about 2500×g. In another embodiment, the separation force includes more than one centrifugations. The first centrifugation can be at a speed of at least 2000×g and a second centrifugation can be at a speed of at least 2000×g.

The blood sample can also be exposed to a separation force for a determinate period of time. The determinate period of time can include, but is not limited to, the time of the centrifugation. The determinate period of time can be sufficient to allow separation of the blood according to density and size. In one embodiment, the determinate period of time can be sufficient to allow separation of the blood into a density gradient. In another embodiment, the determinate period of time can be sufficient to allow separation of the blood into a gradient of plasma, fibrin and blood cells. In yet another embodiment, the determinate period of time can be sufficient to allow separation of the blood into a gradient of plasma, aggregated fibrin and blood cells. Moreover, the determinate period of time can be a time of less than 1 min or at least about 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, 65 mins, 70 mins, 75 mins, 80 mins, 85 mins, 90 mins, 95 mins, 100 mins or greater, or any amount of time in between. In an exemplary embodiment, the determinate period of time the blood sample can be exposed to the separation force can be at least about 5 mins. In another exemplary embodiment, the determinate period of time the blood sample is exposed to the separation force can be at least about 10 mins. In yet another exemplary embodiment, the determinate period of time the blood sample is exposed to the separation force can be at least about 15 mins.

After separation of the blood, the fibrin construct can be harvested. The fibrin construct, as described herein, can include multiple components with distinct features. In one embodiment, the construct can include aggregated fibrin and blood cells. The blood cells can further include platelets, white blood cells, and/or red blood cells.

In an exemplary embodiment, the fibrin construct can be obtained by collecting whole blood in a borosilicate glass container. The blood can be exposed to an anti-coagulant, such as ACD-A, to prevent premature coagulation. A coagulation activator, such as calcium chloride, can then be mixed with the whole blood to induce coagulation and the blood sample mixture can be exposed to a single centrifugation. The centrifugation speed can be in the range of about 2000×g to 5000×g, e.g. about 3000×g for about 15 mins. After centrifugation, the fibrin construct can be harvested and, optionally, modified, e.g. trimmed, blotted, sutured, stretched, compressed, for use.

In a particular embodiment, the fibrin construct can have one side that includes aggregated fibrin, which can be growth factor depleted. As used herein, the term "growth factor depleted" refers to a material, by itself, having little or no biological activity on cells, tissues or organs. FIG. 3 schematically illustrates the fibrin layer 100 as the growth factor depleted side 400 of the construct. In one embodiment, the growth factor depleted surface of the fibrin construct can be substantially lacking growth factors. In another embodiment, the growth factor depleted surface of the fibrin construct can be substantially lacking cells. The growth factor depleted surface can also be substantially lacking in blood cells, such as red blood cells, white blood cells, platelets. In one embodiment, the growth factor depleted surface can be substantially lacking in red blood cells. In another embodiment, the growth factor depleted surface can include blood cells, such as white blood cells and platelets. In an exemplary embodiment, the growth factor depleted surface can include white blood cells.

The other side of the fibrin construct can include a growth factor enriched surface with blood cells. As used herein, the term "growth factor enriched" refers to a material having biological activity that can interact with or have a biological effect on cells, tissues or organs. The growth factor enriched surface can include concentrated blood cells. The growth factor enriched surface can include platelets, white blood cells, and/or red blood cells, where the platelets can further include unactivated and activated platelets. The growth factor enriched surface resides on one side of the fibrin construct and can include substantially all the platelets and growth factors or at least about 50%, 60%, 70%, 80%, 85%, 90%, 95%, 99% of the platelets and growth factors. The growth factor enriched layer may not be integrated into the fibrin layer and may be rubbed off upon harsh handling. In one embodiment, the growth factor enriched surface can selectively include platelets, and/or white blood cells, where the platelets can further include unactivated and activated platelets, and the growth factor enriched surface can be substantially lacking in red blood cells. FIG. 3 further schematically illustrates the platelet/white blood cell/growth factor layer 200 and the red blood cell layer 300 as part of the growth factor enriched side 500 of the construct.

As described above, the fibrin construct can have a growth factor enriched surface concentrated with blood cells and an opposed growth factor depleted surface that is substantially lacking in blood cells, such as red blood cells. The term "substantially," as used herein, means more than about 50%, or more than about 75%, or more than about 85%, or more than about 90%, or more than about 95% is removed. The phrase "substantially lacking" means that there is more than about 50% of the blood cells in the sample have been removed. In exemplary embodiments, more than about 75%, more than about 85%, more than about 90%, or more than about 95% of the blood cells are removed.

Figure 4A:
FIG. 4A shows the removal of the blood cell cap from the fibrin layer.
Figure 4B:
FIG. 4B shows the removal of the blood cell cap from the fibrin layer.

In another embodiment, after separation and harvest of the aggregated fibrin and blood cells, the blood cells can be substantially removed from the aggregated fibrin. The remaining fibrin construct can include aggregated fibrin, which is growth factor depleted and exposed on both sides of the construct. FIGS. 4A and 4B show the removal of the blood cell cap, which includes the removal of platelets, white blood cells and red blood cells from the fibrin layer. By substantially removing the cell layers, the resulting fibrin layer 100 can be separated from the growth factor enriched surface 500 and can include the substantially growth factor depleted surface 400.

Moreover, the fibrin construct can include platelets that are capable of releasing at least one growth factor. In one embodiment, the growth factor enriched surface can include unactivated and/or activated platelets that are capable of releasing at least one growth factor. In an exemplary embodiment, the fibrin construct can be a platelet enriched fibrin construct. In another embodiment, the platelet enriched fibrin construct can include unactivated platelets. In yet another embodiment, the platelet enriched fibrin construct can include activated and unactivated platelets. In one more embodiment, the platelet enriched fibrin construct can include platelets capable of releasing at least one growth factor.

The fibrin construct can also include chemicals released by the blood cells, such as small molecules, glycoproteins, growth factors, cytokines and chemokines. The chemicals can include, but are not limited to, bioactive lipids, bioactive amines, bioactive nucleosides/nucleotides, transforming growth factor (TGF-β1), heparin-binding epidermal-like growth factor (HBGF), platelet-derived growth factor (PDGF-αβ), insulin-like growth factor (IGF), bone morphogenic protein (BMP), and vascular endothelial growth factor (VEGF). In a particular embodiment, the fibrin construct can include a chemical gradient, such as a growth factor gradient. The growth factor gradient can range from substantially lacking in growth factors on the growth factor depleted surface to growth factors substantially present on the growth factor enriched surface. The growth factors can be present in a concentration, either total concentration or individual concentration, of at least about 0.01 pg/μl, 0.02 pg/μl, 0.03 pg/μl, 0.04 pg/μl, 0.05 pg/μl, 0.06 pg/μl, 0.07 pg/μl, 0.08 pg/μl, 0.09 pg/μl, 0.1 pg/μl, 0.2 pg/μl, 0.3 pg/μl, 0.4 pg/μl, 0.5 pg/μl, 0.6 pg/μl, 0.7 pg/μl, 0.8 pg/μl, 0.9 pg/μl, 1.0 pg/μl, 1.1 pg/μl, 1.2 pg/μl, 1.3 pg/μl, 1.4 pg/μl, 1.5 pg/μl, 1.6 pg/μl, 1.7 pg/μl, 1.8 pg/μl, 1.9 pg/μl, 2.0 pg/μl, 2.5 pg/μl, 3.0 pg/μl, 3.5 pg/μl, 4.0 pg/μl, 4.5 pg/μl, 5.0 pg/μl, 5.5 pg/μl, 6.0 pg/μl, 6.5 pg/μl, 7.0 pg/μl, 7.5 pg/μl, 8.0 pg/μl, 8.5 pg/μl, 9.0 pg/μl, 9.5 pg/μl, 10.0 pg/μl, 10.5 pg/μl, 11.0 pg/μl, 11.5 pg/μl, 12.0 pg/μl, 12.5 pg/μl, 13.0 pg/μl, 13.5 pg/μl, 14.0 pg/μl, 14.5 pg/μl, 15.0 pg/μl, 15.5 pg/μl, 16.0 pg/μl, 16.5 pg/μl, 17.0 pg/μl, 17.5 pg/μl, 18.5 pg/μl, 19.0 pg/μl, 19.5 pg/μl, 20 pg/μl, 21 pg/μl, 22 pg/μl, 23 pg/μl, 24 pg/μl, 25 pg/μl, 26 pg/μl, 27 pg/μl, 28 pg/μl, 29 pg/μl, 30 pg/μl, 31 pg/μl, 32 pg/μl, 33 pg/μl, 34 pg/μl, 35 pg/μl, 36 pg/μl, 37 pg/μl, 38 pg/μl, 39 pg/μl, 40 pg/μl, 41 pg/μl, 42 pg/μl, 43 pg/μl, 44 pg/μl, 45 pg/μl, 46 pg/μl, 47 pg/μl, 48 pg/μl, 49 pg/μl, 50 pg/μl, 51 pg/μl, 52 pg/μl, 53 pg/μl, 54 pg/μl, 55 pg/μl, 56 pg/μl, 57 pg/μl, 58 pg/μl, 59 pg/μl, 60 pg/μl, 61 pg/μl, 62 pg/μl, 63 pg/μl, 64 pg/μl, 65 pg/μl, 66 pg/μl, 67 pg/μl, 68 pg/μl, 69 pg/μl, 70 pg/μl, 71 pg/μl, 72 pg/μl, 73 pg/μl, 74 pg/μl, 75 pg/μl, 76 pg/μl, 77 pg/μl, 78 pg/μl, 79 pg/μl, 80 pg/μl, 85 pg/μl, 90 pg/μl, 95 pg/μl, 100 pg/μl, 105 pg/μl, 110 pg/μl, 115 pg/μl, 120 pg/μl, 130 pg/μl, 140 pg/μl, 150 pg/μl, 160 pg/μl, 170 pg/μl, 180 pg/μl, 190 pg/μl, 200 pg/μl, 225 pg/μl, 250 pg/μl, 275 pg/μl, 300 pg/μl, 325 pg/μl, 350 pg/μl, 375 pg/μl, 400 pg/μl, 425 pg/μl, 450 pg/μl, 475 pg/μl, 0.5 ng/μl, 0.6 ng/μl, 0.7 ng/μl, 0.8 ng/μl, 0.9 ng/μl, 1.0 ng/μl, 1.1 ng/μl, 1.2 ng/μl, 1.3 ng/μl, 1.4 ng/μl, 1.5 ng/μl, 1.6 ng/μl, 1.7 ng/μl, 1.8 ng/μl, 1.9 ng/μl, 2.0 ng/μl, 2.5 ng/μl, 3.0 ng/μl, 3.5 ng/μl, 4.0 ng/μl, 4.5 ng/μl, 5.0 ng/μl, 5.5 ng/μl, 6.0 ng/μl, 6.5 ng/μl, 7.0 ng/μl, 7.5 ng/μl, 8.0 ng/μl, 8.5 ng/μl, 9.0 ng/μl, 9.5 ng/μl, 10.0 ng/μl, 10.5 ng/μl, 11.0 ng/μl, 11.5 ng/μl, 12.0 ng/μl, 12.5 ng/μl, 13.0 ng/μl, 13.5 ng/μl, 14.0 ng/μl, 14.5 ng/μl, 15.0 ng/μl, 15.5 ng/μl, 16.0 ng/μl, 16.5 ng/μl, 17.0 ng/μl, 17.5 ng/μl, 18.5 ng/μl, 19.0 ng/μl, 19.5 ng/μl, 20 ng/μl, 21 ng/μl, 22 ng/μl, 23 ng/μl, 24 ng/μl, 25 ng/μl, 26 ng/μl, 27 ng/μl, 28 ng/μl, 29 ng/μl, 30 ng/μl, 31 ng/μl, 32 ng/μl, 33 ng/μl, 34 ng/μl, 35 ng/μl, 36 ng/μl, 37 ng/μl, 38 ng/μl, 39 ng/μl, 40 ng/μl, 41 ng/μl, 42 ng/μl, 43 ng/μl, 44 ng/μl, 45 ng/μl, 46 ng/μl, 47 ng/μl, 48 ng/μl, 49 ng/μl, 50 ng/μl, 51 ng/μl, 52 ng/μl, 53 ng/μl, 54 ng/μl, 55 ng/μl, 56 ng/μl, 57 ng/μl, 58 ng/μl, 59 ng/μl, 60 ng/μl, 61 ng/μl, 62 ng/μl, 63 ng/μl, 64 ng/μl, 65 ng/μl, 66 ng/μl, 67 ng/μl, 68 ng/μl, 69 ng/μl, 70 ng/μl, 71 ng/μl, 72 ng/μl, 73 ng/μl, 74 ng/μl, 75 ng/μl, 76 ng/μl, 77 ng/μl, 78 ng/μl, 79 ng/μl, 80 ng/μl, 85 ng/μl, 90 ng/μl, 95 ng/μl, 100 ng/μl, 105 ng/μl, 110 ng/μl, 115 ng/μl, 120 ng/μl, 130 ng/μl, 140 ng/μl, 150 ng/μl, 160 ng/μl, 170 ng/μl, 180 ng/μl, 190 ng/μl, 200 ng/μl, 225 ng/μl, 250 ng/μl, 275 ng/μl, 300 ng/μl, 325 ng/μl, 350 ng/μl, 375 ng/μl, 400 ng/μl, 425 ng/μl, 450 ng/μl, 475 ng/μl, 500 ng/μl, or greater, or any concentration of growth factor in between. In an exemplary embodiment, the total concentration of growth factors can be at least about 1.0 pg/μl. In another exemplary embodiment, the total concentration of growth factors can be at least about 5.0 pg/μl. In yet another exemplary embodiment, the total concentration of growth factors can be at least about 10.0 pg/μl. In an additional exemplary embodiment, the total concentration of growth factors can be at least about 50.0 pg/μl. In one embodiment, an individual concentration of a growth factor, such as PDGF-αβ or VEGF, can be at least about 0.1 pg/μl. In another exemplary embodiment, the individual concentration of a growth factor can be at least about 1.0 pg/μl. In yet another exemplary embodiment, the individual concentration of a growth factor can be at least about 5.0 pg/μl.

In one embodiment, one side of the growth factor enriched surface (500, see FIG. 3) of the fibrin construct can, optionally, include a slightly growth factor enriched region, which can be represented by the layer 200 in FIG. 3. The term "slightly," as used herein, means less than about 50%, or less than about 25%, or less than about 15%, or less than about 10%, or less than about 5% of the original growth factor enriched surface is present. The phrase "slightly" means that there is less than about 50% of the original growth factor enriched surface is present. In exemplary embodiments, less than about 25%, less than about 15%, less than about 10%, or less than about 5% of the original growth factor enriched surface can be present. The slightly growth factor enriched region can include white blood cells and/or platelets found in layer 200 of FIG. 3, where the platelets can further include unactivated and activated platelets. The slightly growth factor enriched region can also include a layer with a portion of the white blood cell/platelet layer 200, where a portion of the platelet/white blood cell/growth factor layer has been removed and a portion of the platelet/white blood cell/growth factor layer remains in the growth factor enriched surface 500 of the fibrin construct. The growth factor enriched surface 500 can further be substantially lacking in red blood cells, or the red blood cell layer 300 can be removed from the fibrin construct. In an exemplary embodiment, the growth factor enriched surface 500 can include at least a portion of the unactivated platelets in the platelet/white blood cell/growth factor layer. In another exemplary embodiment, the fibrin construct can have a growth factor enriched surface 500 that is substantially lacking in red blood cells, e.g. the red blood cells layer 300 is substantially removed.

In another embodiment, the fibrin construct can include a blood cell gradient. The blood cell gradient can range from substantially lacking in blood cells on the growth factor depleted surface to blood cells substantially present on the growth factor enriched surface. The fibrin construct can, optionally, include a white blood cell gradient. The white blood cell gradient can range from substantially lacking in white blood cells on the growth factor depleted surface to white blood cells substantially present on the growth factor enriched surface. The fibrin construct can, optionally, include a platelet gradient. The platelet gradient can range from substantially lacking in platelet on the growth factor depleted surface to platelet substantially present on the growth factor enriched surface.

In one aspect, the fibrin construct is dimensionally stable. The term "dimensionally stable," as used herein, refers to a material having relatively constant dimensions, durability under stress, and resiliency. Moreover, the fibrin construct can be capable of being punctured, such as for suturing, and retaining its dimensional stability. It can also be folded, layered with one or more additional fibrin constructs, and blotted, all without destroying the mechanical integrity of the fibrin construct.

In one embodiment, the dimensionally stable fibrin construct can have a resiliency that is defined by elongation at break strength, ultimate strength and compression strength. The elongation at break strength of the fibrin construct can be greater than about 100% or at least about 110%, 120%, 130%, 140%, 150%, 160%, 170%, 180%, 190%, 200%, 210%, 220%, 230%, 240%, 250%, 260%, 270%, 280%, 290%, 300%, 350%, 400%, 450%, 500%, or greater or any break strength in between. In one embodiment, the elongation at break strength of the dimensionally stable fibrin construct is at least about 200%.

The ultimate strength of the dimensionally stable fibrin construct can be greater than about 0.1 MPa, or at least about 0.11 MPa, 0.12 MPa, 0.13 MPa, 0.14 MPa, 0.15 MPa, 0.16 MPa, 0.17 MPa, 0.18 MPa, 0.19 MPa, 0.2 MPa, 0.25 MPa, 0.3 MPa, 0.35 MPa, 0.4 MPa, 0.45 MPa, 0.5 MPa, or greater or any ultimate strength in between. In one embodiment, the ultimate strength of the dimensionally stable fibrin construct is at least about 0.15 MPa.

The compression strength of the dimensionally stable fibrin construct can be greater than about 10 kPa, or at least about 11 kPa, 12 kPa, 13 kPa, 14 kPa, 15 kPa, 16 kPa, 17 kPa, 18 kPa, 19 kPa, 20 kPa, 21 kPa, 22 kPa, 23 kPa, 24 kPa, 25 kPa, 26 kPa, 27 kPa, 28 kPa, 29 kPa, 30 kPa, 31 kPa, 32 kPa, 33 kPa, 34 kPa, 35 kPa, 36 kPa, 37 kPa, 38 kPa, 39 kPa, 40 kPa, 41 kPa, 42 kPa, 43 kPa, 44 kPa, 45 kPa, 46 kPa, 47 kPa, 48 kPa, 49 kPa, 50 kPa, or greater or any compression strength in between. In one embodiment, the compression strength of the dimensionally stable fibrin construct is at least about 30 kPa.

In an exemplary embodiment, the fibrin construct can have a growth factor enriched surface and a growth factor depleted surface. The growth factor enriched surface can be concentrated with blood cells and platelets, where the platelets and/or blood cells can be capable of releasing at least one growth factor. The growth factor depleted surface can be substantially lacking in blood cells and platelets and includes aggregated fibrin. The fibrin construct can also be dimensionally stable, such that the fibrin construct can be sutured, stapled, trimmed, blotted, stretched and compressed, while maintaining many of its desirable properties relevant to wound healing.

Optional Components

The fibrin construct may comprise optional components that can be added during or after preparing the fibrin construct. Thus, in addition to fibrin and/or blood cells, the fibrin construct can include a fibrinolysis inhibitor, a plasmin inhibitor, e.g. aprotinin, aprilotinin, alpha-2-antiplasmin, alpha-2-macroglobulin, alpha-1-antitrypsin, epsilon-aminocaproic acid or tranexamic acid, or a plasmin activator inhibitor, e.g. PAI-1 or PAI-2.

The fibrin constructs can be treated with additives or drugs prior to implantation, e.g., to promote the formation of new tissue after implantation. Thus, for example, stem cells, growth factors, cytokines, extracellular matrix components, and other bioactive materials can be added to the substrate to promote healing and formation of new tissue. Such additives can in general be selected according to the target site, tissue or organ being reconstructed or augmented, to ensure that appropriate new tissue is formed at the target site (for examples of such additives for use in promoting bone healing, see, e.g., Kirker-Head, C. A. Vet. Surg. 24 (5): 408-19 (1995)). For example, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), stromal cell derived factor, insulin-like growth factor (IGF), transforming growth factor (TGF-β1), platelet-derived growth factor (PDGF-αβ), macrophage inflammatory proteins 1 alpha (MIP-1 alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-alpha, and TNF-beta, leptin, leukemia inhibitory factor (LIF), endostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, cytokines, genes, proteins, and the like) can be added in amounts in excess of any amount of such growth factors (if any) which may be produced by the cells seeded on the substrate. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

Growth factors and regulatory factors can be added to the fibrin constructs to enhance, alter or modulate proliferation and cell maturation and differentiation of cells at the target site. The growth and activity of cells can be affected by a variety of growth factors such as growth hormone, somatomedins, colony stimulating factors, erythropoietin, epidermal growth factor, hepatic erythropoietic factor (hepatopoietin), and like. Other factors which regulate proliferation and/or differentiation include prostaglandins, interleukins, and naturally-occurring chalones.

A "therapeutically effective amount" or "effective amount" is that amount of an agent to achieve a pharmacological effect. The term "therapeutically effective amount" includes, for example, a prophylactically effective amount. An "effective amount" is an amount effective to achieve a desired pharmacologic effect or therapeutic improvement without undue adverse side effects. For example, an effective amount refers to an amount that increases operativity, or increases weight bearing load, or decreases pain, or increases growth in the bone and cartilage of one or more joints, or reduces joint distortion, pain, swelling, or stiffness. The effective amount of a agent will be selected by those skilled in the art depending on the particular patient and the disease level. It is understood that "an effect amount" or "a therapeutically effective amount" can vary from subject to subject, due to variation in metabolism of therapeutic agents and/or prokinetic agents, age, weight, general condition of the subject, the condition being treated, the severity of the condition being treated, and the judgment of the prescribing physician.

The fibrin constructs can be used to deliver one or more therapeutic agents to a desired location. The fibrin constructs can be used to deliver therapeutic agents to an in vivo location, an in vitro location, or other locations. The fibrin constructs can be administered to these locations using any method. Alternatively, the fibrin constructs including platelets and growth factors can be implanted in a body and used to deliver molecules produced by the platelets after implantation.

Release kinetics in some embodiments can be manipulated by cross-linking the fibrin constructs through any means. In some embodiments, cross-linking will alter, for example, the rate at which the fibrin construct degrades or the rate at which a compound is released from the fibrin construct by increasing structural rigidity and delaying subsequent dissolution of the fibrin construct. The fibrin construct can be formed in the presence of cross-linking agents or can be treated with cross-linking agents. Any technique for cross-linking materials may be used as known to one of ordinary skill in the art. Examples of cross-linking agents include, but are not limited to, condensing agents such as aldehydes e.g., glutaraldehyde, carbodiimide EDC (1-ethyl-3(3 dimethyl aminopropyl)), photosensitive materials that cross-link upon exposure to specific wavelengths of light, osmium tetroxide, carbodiimide hydrochloride, and NHS (n-hydroxysuccinimide).

The release kinetics of the fibrin constructs can also be controlled by manipulating the physical and chemical composition of the fibrin constructs. For example, small fibers of fibrin are more susceptible to hydrolysis than larger diameter fibers of fibrin. An agent delivered within a fibrin construct composed of smaller fibers is released more quickly than when prepared within a construct composed of larger diameter fibers.

The fibrin constructs can also be treated with a coating or permeated with a material to alter its mechanical properties. The coating can refer to coating or permeating the fibrin construct with a material such as, liquefied copolymers (poly-DL-lactide co-glycolide 50:50 80 mg/ml methylene chloride). Coating may be performed in one layer, or multiple layers until the desired mechanical properties are achieved.

The fibrin constructs can also be treated or seeded with various factors and proteins to control the degradation/absorption of the composition in the subject. For instance, if new cells may be slow growing, then it is beneficial to maintain the construct integrity for a long enough period of time to allow the new cells enough time to regenerate and grow. On the other hand, if the new cells are able to quickly reproduce and grow, then a short lived construct could be desirable. Varying the concentration of aprotinin additives, aminocaproic acid, tranxemic acid, or similar fibrinolytic inhibitors or the degree of chemical cross-linking in the construct could be used to precisely control this variable. The fibrin construct could also be seeded with varying growth factors such as angiogenesis factor to promote a growth of blood vessels upon implantation.

In one embodiment, the fibrin construct can be co-administered with another component, such as an additional growth factor, via delivery in the same construct. By "co-administered" is meant simultaneous administration in the same formulation or in two different formulations that are combined into one formulation for administration. One or multiple components can be co-administered with the fibrin construct. For example, the fibrin construct can further include a growth factor such as vascular endothelial growth factor (VEGF), epidermal growth factor (EGF), heparin-binding epidermal-like growth factor (HBGF), and fibroblast growth factor (FGF). The fibrin construct can also include fibrinolysis inhibitor, a plasmin inhibitor, aprotinin, aprilotinin, alpha-2-antiplasmin, alpha-2-macroglobulin, alpha-1-antitrypsin, epsilon-aminocaproic acid or tranexamic acid, and a plasmin activator inhibitor. In another embodiment, the fibrin construct can include a cross-linking agent, such as a condensing agent, a photosensitive material, an aldehyde, glutaraldehyde, and carbodiimide EDC (1-ethyl-3(3 dimethyl aminopropyl).

Fibrin Construct Dimensions

The dimensions of the fibrin construct can be dependent on multiple factors, such as the volume of the blood sample, the amount of fibrinogen and/or aggregated fibrin present in the blood sample, the size of the container, the amount of separation force used, the amount of time the blood sample is exposed to the separation force and any modifications of the fibrin construct made during harvest, i.e. removal of blood cells or the growth factor enriched surface. Varying one or more of the parameters can change the dimensions of the fibrin construct. For example, using a greater volume of blood in a narrow container can yield a long, narrow fibrin construct.

Figure 5B:
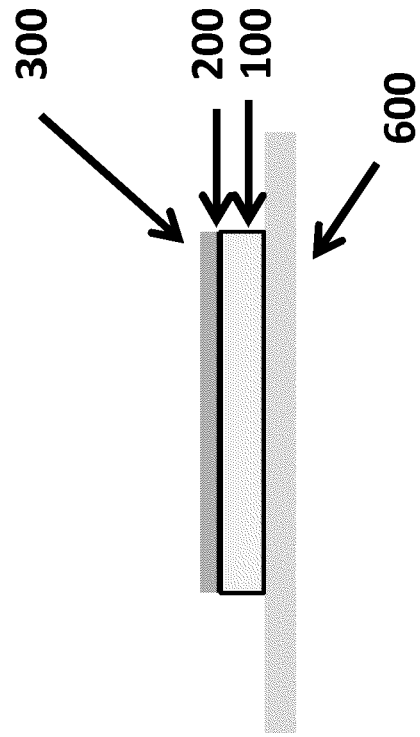
FIG. 5B shows a schematic cross-section of the PEFC on the gauze pad.
Figure 5A:
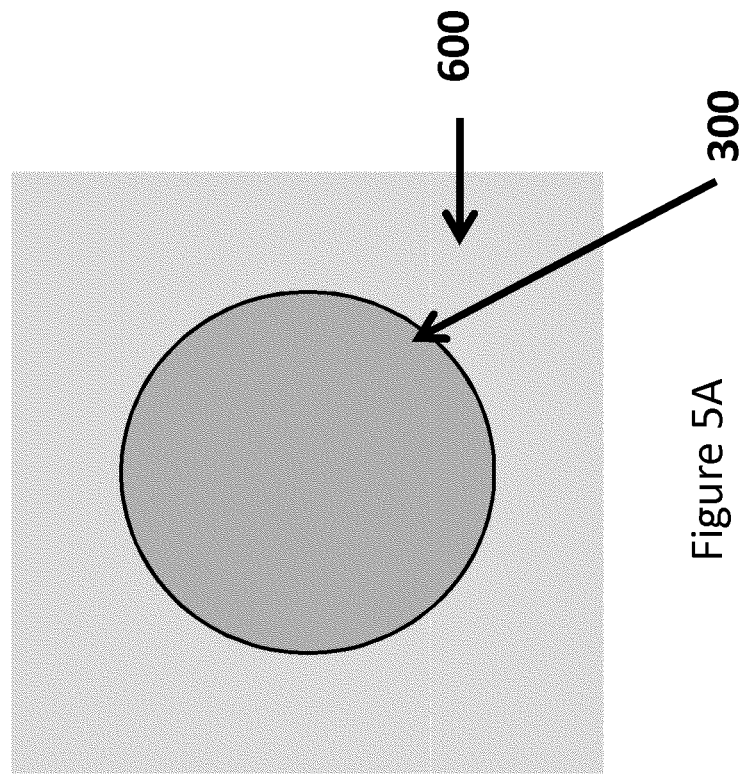
FIG. 5A shows a schematic top view of a PEFC on a flat gauze pad (shaded square 600)

The fibrin constructs can also be shaped into a structure with length and diameter dimensions selected to correspond to the target site in the subject. The fibrin constructs can be folded, layered, stretched, compressed, trimmed or blotted to alter the size of the construct. The fibrin constructs can be blotted on and/or between absorbent materials, such as gauze, 600, to remove excess plasma, serum or liquid in the fibrin construct, as shown in FIGS. 5A and 5B. Moreover, blotting the fibrin construct can also reduce the size of the fibrin construct, such as making the construct thinner, without trimming or cutting the fibrin construct.

Figure 6:
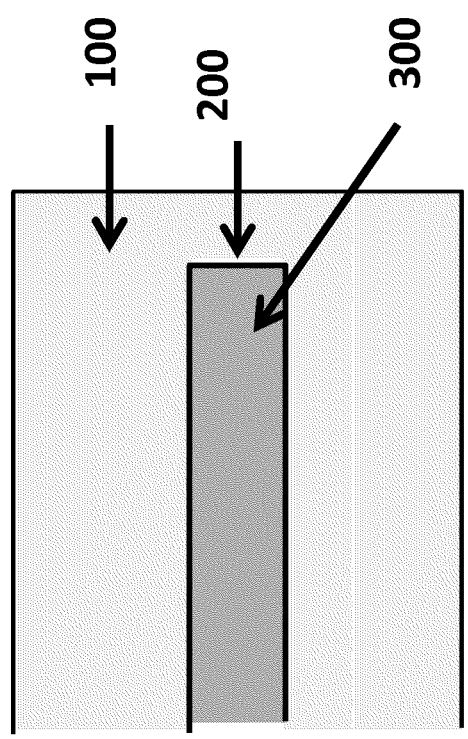
FIG. 6 shows a schematic of a fibrin construct folded in half to protect the growth factor enriched layer.

The fibrin construct can also be enlarged by joining, layering or bonding multiple constructs together using standard techniques such as suturing, heating, stapling, and gluing with biological glue, or a combination of these methods. The fibrin construct can also be joined or bonded to a target site in the subject. Joining, folding, layering or bonding one or more constructs together can also protect one or more sides of the construct. In one embodiment, the fibrin construct is folded in half upon itself so that adjacent halves of the fibrin construct contact each other and form an inner portion of the folded construct. Folding the fibrin construct can protect one side of the fibrin construct, such as the growth factor enriched layer or slightly growth factor enriched region, the platelet/WBC/growth factor layer 200 and, optionally, the RBC layer 300, while the other side of the fibrin construct, the growth factor depleted surface, the fibrin layer 100 forms an outer portion of the folded construct, as shown in FIG. 6. Furthermore, the folded construct can be joined or bonded together, such as through suturing, heating, stapling, and gluing, along an edge of the construct to secure the construct in a folded condition.

Figure 7:
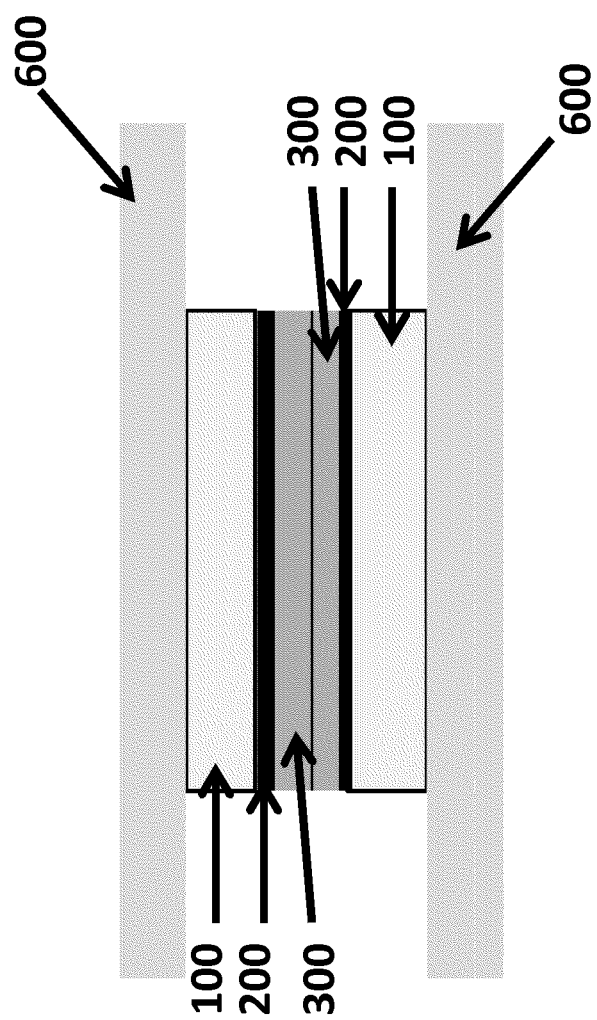
FIG. 7 shows a schematic cross-section of a multi-layered PEFC blotted between two pieces of gauze.
Figure 8:
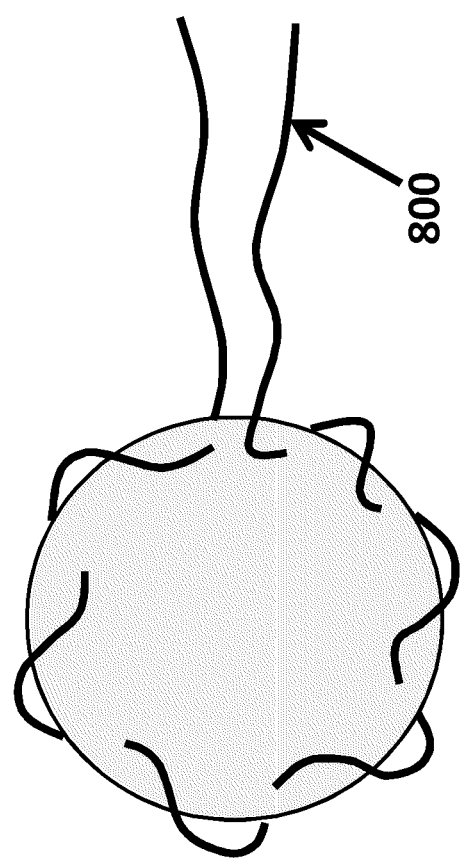
FIG. 8 shows a schematic top view of the multi-layered PEFC sutured along the edge.

In another embodiment, the fibrin construct can be a multilayered construct. Two or more fibrin constructs can be joined together with one side of one fibrin construct facing a side of the other fibrin construct, such as the growth factor enriched surfaces 500, e.g. the platelet/WBC/growth factor layers 200 and, optionally, the RBC layers 300 form an inner portion of the multilayered construct, as shown in FIG. 7. The other sides of the fibrin construct, such as the growth factor depleted surface 400 including the fibrin layers 100, can form the outer portions of the multilayered construct. The multilayered construct can further be joined or bonded together, such as through joining with sutures 800 along an outer portion of an edge to secure the multilayered construct, as shown in FIG. 8. Other configurations of the multilayered construct can also be used, such as growth factor enriched surface 500 to growth factor enriched surface 500, growth factor enriched surface 500 to growth factor depleted surface 400 and growth factor depleted surface 400 to growth factor depleted surface 400. In addition, when more than two fibrin constructs are layered, variations in layering can also be useful, such as growth factor enriched surface 500 to growth factor enriched surface 500 to growth factor depleted surface 400, growth factor enriched surface 500 to growth factor depleted surface 400 to growth factor depleted surface 400, growth factor depleted surface 400 to growth factor depleted surface 400 to growth factor enriched surface 500 and any other possible variation obtained from layering multiple fibrin constructs.

In yet another embodiment, the fibrin construct can be multilayered with each individual fibrin construct being a distinct component of the multilayer. For example, one or more of the fibrin constructs can include one or more additional components and/or altered growth factor enriched surfaces 500, e.g. slightly growth factor enriched region by substantially removing the blood cell layer 300. In this embodiment, one fibrin construct of the multilayer includes an individual layer with a growth factor enriched surface 500 and a pharmaceutical composition, e.g. one or more drugs. The fibrin construct can be varied in the individual layers and/or an additional component can differ in the alternating layers. In another embodiment, the orientation of the fibrin constructs with respect to one another can be varied, e.g. the growth factor enriched surfaces 500 can face one another or the growth factor depleted surfaces 400 can face one another or the growth factor enriched surface 500 of one fibrin construct can face the growth factor depleted surface 400 of another construct, or any variation thereof. In another embodiment, a fibrin constructs can be altered, oriented, or layered with or without additional components to provide immediate or delayed effect of the growth factor enriched surface 500 to the site of implantation.

Suturing can involve known techniques using absorbable synthetic suture material such as the biocompatible polymer is polyglactin and polyglycolic acid, manufactured as Vicryl™ by Ethicon Co., Somerville, N.J. (See e.g., Craig P. H., Williams J. A., Davis K. W., et al.: A Biological Comparison of Polyglactin 910 and Polyglycolic Acid Synthetic Absorbable Sutures. Surg. 141; 1010, (1975)). One or more fibrin constructs can be joined to one another. Using sutures 800 as shown in FIG. 8, one or more fibrin constructs can be implanted in a tissue site. Other methods of joining involve using biological glues. Biological glues can adhere to tissues, attach them to each other, or attach them to other structures on the body in a few minutes, without using staples or sutures. These glues are eliminated, in general after the cicatrization of the wound, by biodegradation, resorption or by simple detachment in the form of scabs.

Tissue adhesives can also be used to join one or more constructs together. Various technologies have been developed for the formulation of tissue adhesives. Some of them are of synthetic origin, such as the glues based on cyanoacrylates (2-butyl cyanoacrylate, 2-octyl cyanoacrylate), or on synthetic polymers, and others contain biological materials such as collagen or fibrin (See e.g., U.S. Pat. Nos. 5,844,016, 5,874,500; 5,744,545; 5,550,187 and 6,730,299).

Delivery

The fibrin constructs can be used to treat, repair or augment a tissue at a target site such as a wound, an injury or an incision. The terms "treat" or "treatment" refer to any treatment of a wound, lesion, abrasion, incision, or laceration, or wound healing in general or wound healing associated with an invasive medical procedure or surgical intervention; promoting wound healing, e.g., promoting healing of a wound, lesion, abrasion, incision, or laceration, augmenting the subject's natural wound healing process, increasing wound healing in a subject, relieving a condition caused that results in a wound, lesion, abrasion, incision, or laceration, or stopping the symptoms associated with a disease or disorder that inhibits or prevents wound healing.

Methods of delivering the fibrin construct to a target site in the subject can include, but are not limited to, placement of the fibrin construct within or on a target site. The fibrin construct can be held at the target site by methods such as, but not limited to, implantation, suturing and/or gluing the fibrin construct to the target site. Moreover, the fibrin construct can be delivered to the subject epicutaneously, intradermally, subcutaneously, or surgically implanted within a target site. The fibrin construct can be implanted to repair, augment or replace (at least a portion of) a natural tissue of a subject (e.g., for veterinary or medical (human) applications). The term "implantable" means the fibrin construct can be inserted, embedded, grafted or otherwise chronically attached or placed on or in a patient.

The fibrin construct can be delivered to the target site and kept in place at the target site by methods used in the art. Such methods can include, but are not limited to, suturing techniques using absorbable synthetic suture material such as the biocompatible polymer is polyglactin and polyglycolic acid, manufactured as Vicryl™ by Ethicon Co., Somerville, N.J. (See e.g., Craig P. H., Williams J. A., Davis K. W., et al.: A Biological Comparison of Polyglactin 910 and Polyglycolic Acid Synthetic Absorbable Sutures. Surg. 141; 1010, (1975)), staples, joining with biological glues and/or tissue adhesives such as synthetic adhesives, glues based on cyanoacrylates (2-butyl cyanoacrylate, 2-octyl cyanoacrylate), or on synthetic polymers, and others contain biological materials such as collagen or fibrin (See e.g., U.S. Pat. Nos. 5,844,016, 5,874,500; 5,744,545; 5,550,187 and 6,730,299). A person skilled in the art will appreciate that various combinations of such techniques can be used as well.

In an exemplary embodiment, the fibrin construct can be used to treat, repair or augment a tissue at a target site, such as a wound, an injury or an incision, by delivering at least one growth factor and/or platelet. Additionally, the fibrin construct can be delivered to the target site to promote healing by delivering at least one growth factor and/or platelet to the target site. The fibrin construct can be delivered to the subject epicutaneously, intradermally, subcutaneously, or surgically implanted within the target site.

Kits

The methods and compositions encompass kits for wound healing. The kits can comprise a container, such as a borosilicate container, for receiving a blood sample. The kit can further contain a blood collection apparatus, such as a syringe, for receiving a whole blood sample. The syringe can further be adaptable to or removable from the container to collect the blood directly into the container. The syringe can contain be configured to hold a predefined volume of blood. The syringes can contain volumes from about 0.1 ml, 0.2 ml, 0.3 ml, 0.4 ml, 0.5 ml, 0.6 ml, 0.7 ml, 0.8 ml, 0.9 ml, 1.0 ml, 1.5 ml, 2 ml, 2.5 ml, 3 ml, 3.5 ml, 4 ml, 4.5 ml, 5 ml, 5.5 ml, 6 ml, 6.5 ml, 7 ml, 7.5 ml, 8 ml, 8.5 ml, 9 ml, 9.5 ml, 10 ml or more or any derivative therein.

The kit can also contain an anti-coagulant. The anti-coagulant can include, but is not limited to, anticoagulant citrate dextrose solution A (ACD-A), heparin, EDTA, citrate, oxalate, thrombin inhibitors, or other factor inhibitors. The anti-coagulant can be in powder, liquid or lyophilized form. The anti-coagulant can also be included at a concentration and/or amount appropriate for the volume of blood to be collected or the volume blood that can be added to the container. In an exemplary embodiment, the anti-coagulant can be ACD-A.

The kit can also include a coagulation activator, such as an ionic coagulation activator. The coagulation activator can include, but is not limited to, zeolites, hemostatic agents, calcium ions, calcium salts, Factor I, Factor II, Factor III, Factor IV, Factor V, Factor VII, Factor X, Factor XI, Factor XII, Factor XIII, thrombokinase, proaccelerin, proconvertin, antihemophilic globulin, Christmas factor, prothombinase, plasma thromboplastin antecedent, Hageman factor, and fibinase.

The kit can further include a cross-linking agent. The cross-linking agent can include, but is not limited to, a condensing agent, a photosensitive material, an aldehyde, glutaraldehyde, and carbodiimide EDC (1-ethyl-3(3 dimethyl aminopropyl)).

Storage

The fibrin constructs can be stored and used shortly before implantation. The fibrin constructs can be stored in a dry or frozen state. Storage conditions will depend on whether a therapeutic agent is incorporated onto or into the construct and whether the platelets are substantially removed. In embodiments where a therapeutic agent is incorporated, the construct can be stored at temperatures below 0° C., under vacuum, or in a lyophilized state. Other storage conditions can be used, for example, at room temperature, in darkness, in vacuum or under reduced pressure, under inert atmospheres, at refrigerator temperature, in aqueous or other liquid solutions, or in powdered form depending on the materials in and on the construct.

The fibrin constructs may be sterilized through conventional means known to one of skilled in the art such as radiation, and heat. The fibrin constructs can also be combined with bacteriostatic agents, such as thimerosal, to inhibit bacterial growth. In some embodiments, the fibrin constructs can be treated with chemicals, solutions, or processes that confer stability in storage and transport.

Experimental Data

Example 1: Preparation of Platelet Enriched Fibrin Construct (PEFC)

Figure 9:
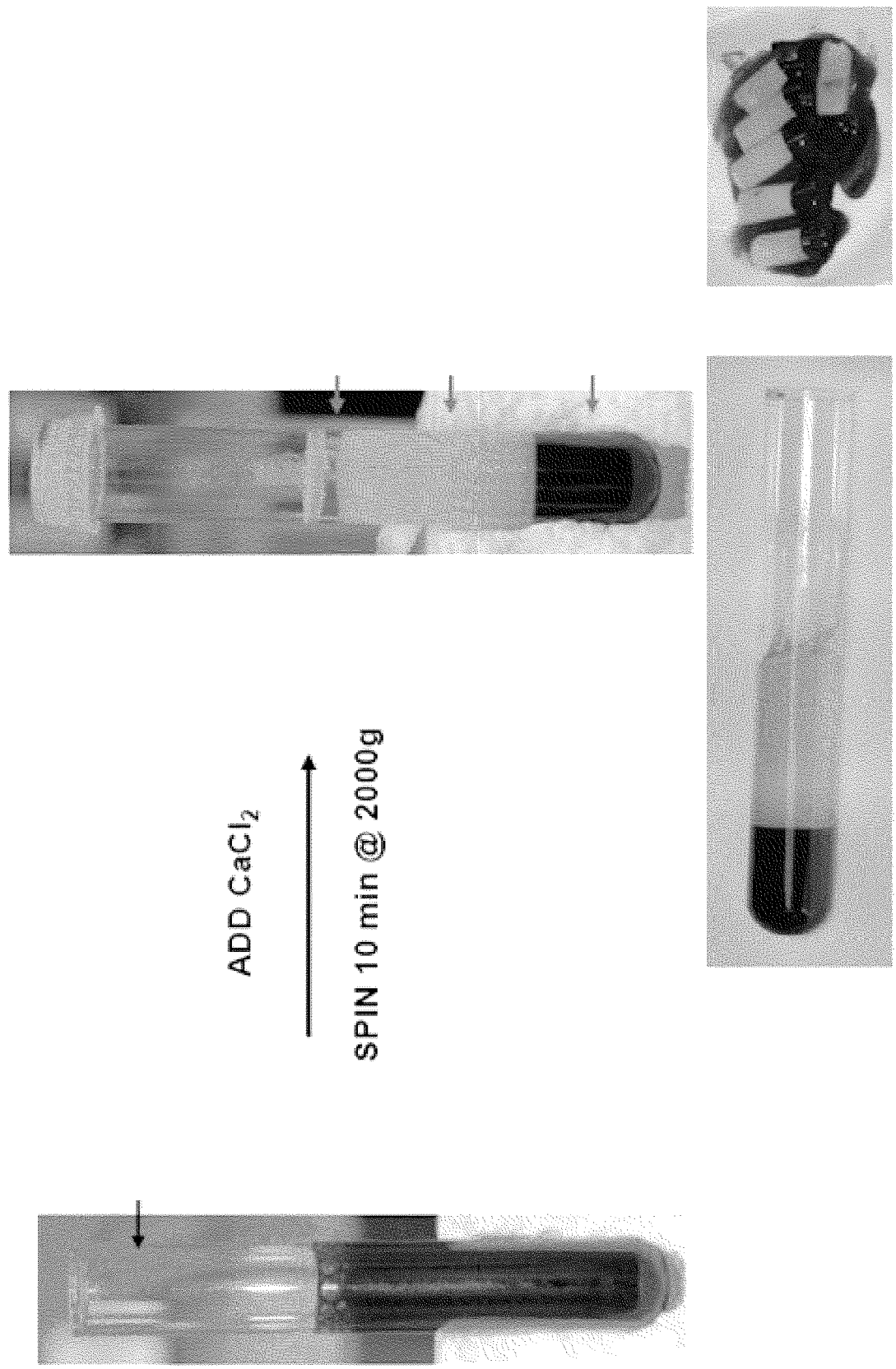
FIG. 9 shows the slow spin (~2000×g) method of preparing the platelet enriched fibrin construct (PEFC)

Soft Spin Preparations:

Bovine blood samples of 6.8 ml were collected and exposed to 1.2 ml of anti-coagulant, ACD-A (15% by volume in final mixture). The blood samples were transferred to borosilicate glass tubes with 180 μl of 1M $CaCl_2$ solution. The samples were inverted 10 times and centrifuged at 2000×g for 10 mins. During centrifugation, the blood sample clotted and separated into distinct layers: a plasma layer (PLASMA), a fibrin plug layer (CLOT) and a blood cell layer (RBC). The images of FIG. 9 sequentially illustrate this procedure.

Figure 4C:
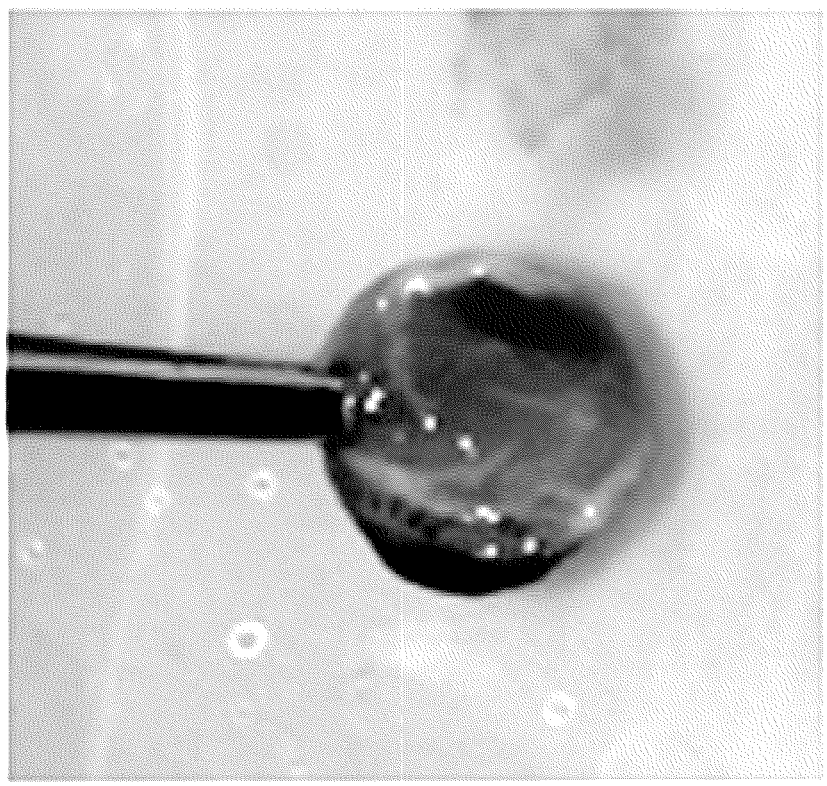
FIG. 4C shows the blood cell cap.
Figure 4D:
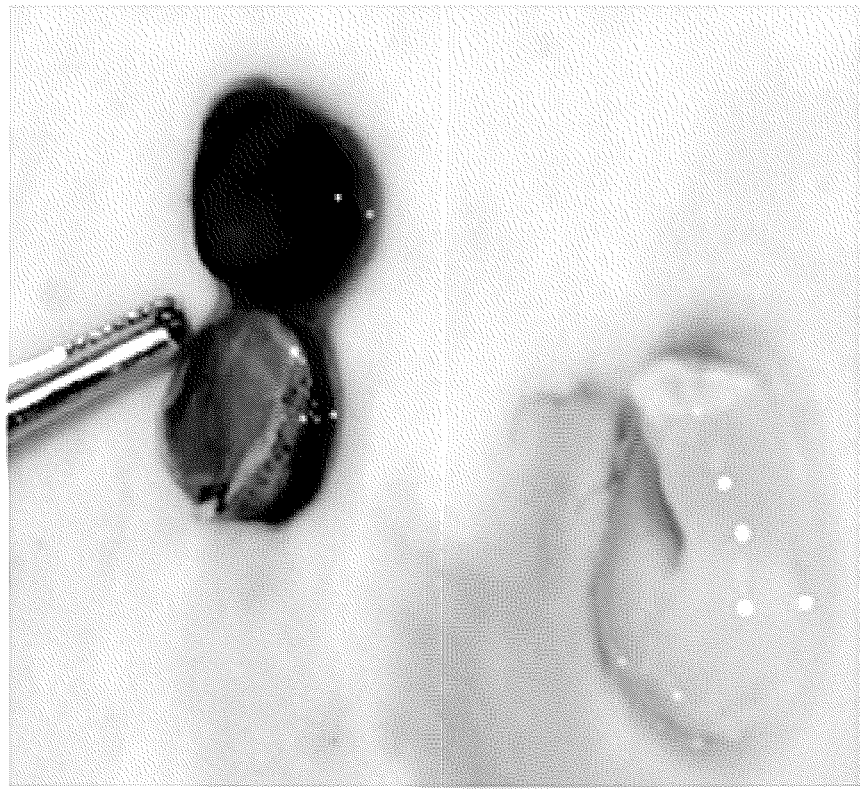
FIG. 4D shows the separated blood cell cap and the fibrin layer.

The blood cell layer can be physically removed by peeling the cap of blood cells, as shown in FIGS. 4A and 4B, from the fibrin layer, resulting in a construct comprising platelet/white blood cells, as shown in FIG. 4C. Also, FIG. 4D illustrates the blood cell cap removed from the fibrin layer. Most of the red blood cells can further be removed by blotting, scraping, etc.

Double Soft Spin:

Similar to the soft spin method, bovine blood samples were collected and exposed to anti-coagulant, ACD-A. The blood samples, 6.8 ml, were transferred to borosilicate glass tubes with 180 μl of 1M $CaCl_2$ solution. The samples were centrifuged at 2000×g for 10 mins and fibrin layer and blood cell layer were removed from the clot. The fibrin plug layer with intact blood cell layer was further centrifuged for a second spin of 2000×g for 10 mins. After centrifugation, the blood cell layer further separated from serum and shrunk in size.

The fibrin plug layer with intact blood cell layer has further been shown to be blottable after soft spinning. Absorbent pads were placed on either side of the construct to remove residual liquid from the construct and the remaining membrane demonstrated significant tactile strength.

Figure 10A:
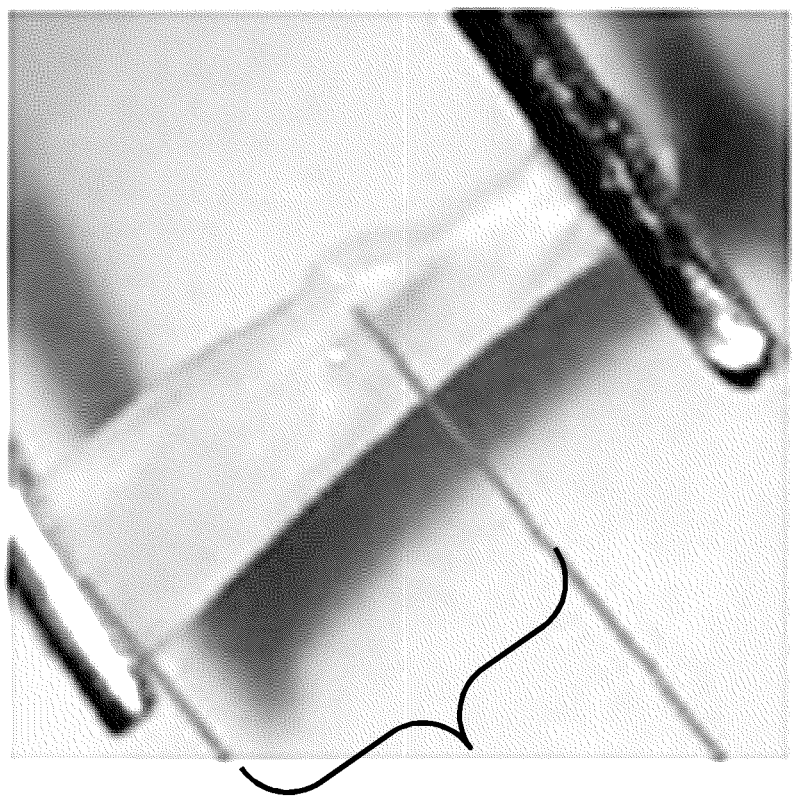
FIG. 10A illustrates the fibrin construct as being stretchable, bracket indicates original length of PEFC.
Figure 10B:
FIG. 10B illustrates the blood cell cap as being suturable.
Figure 10C:
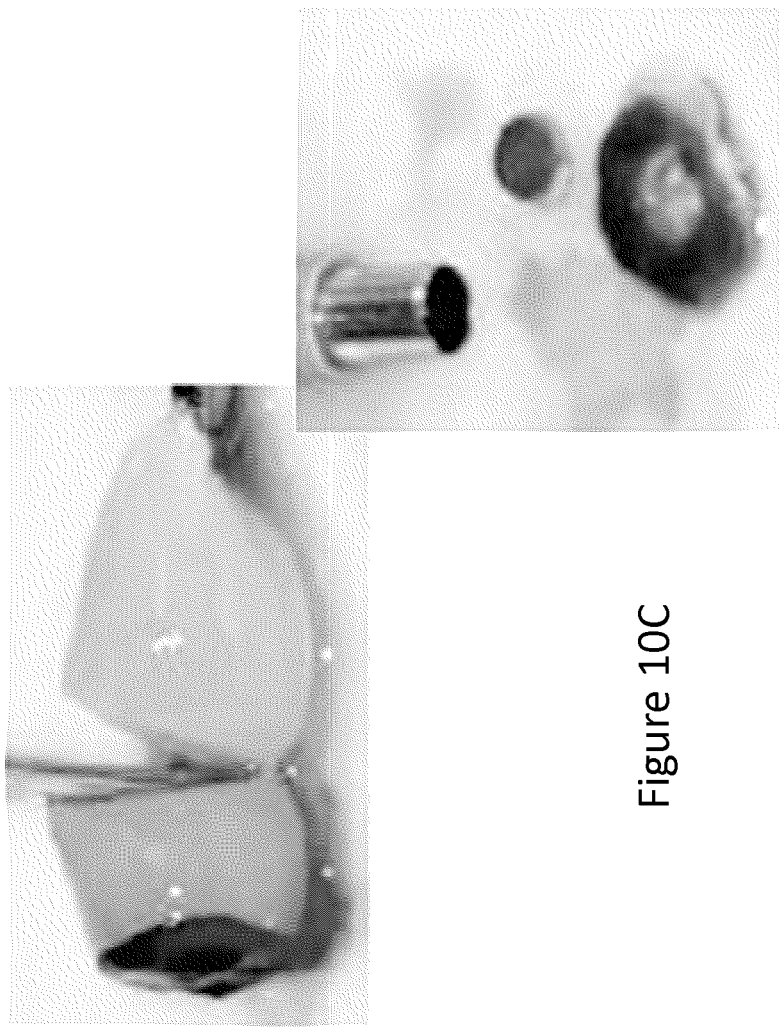
FIG. 10C illustrates the PEFC as being trimmable.
Figure 10D:
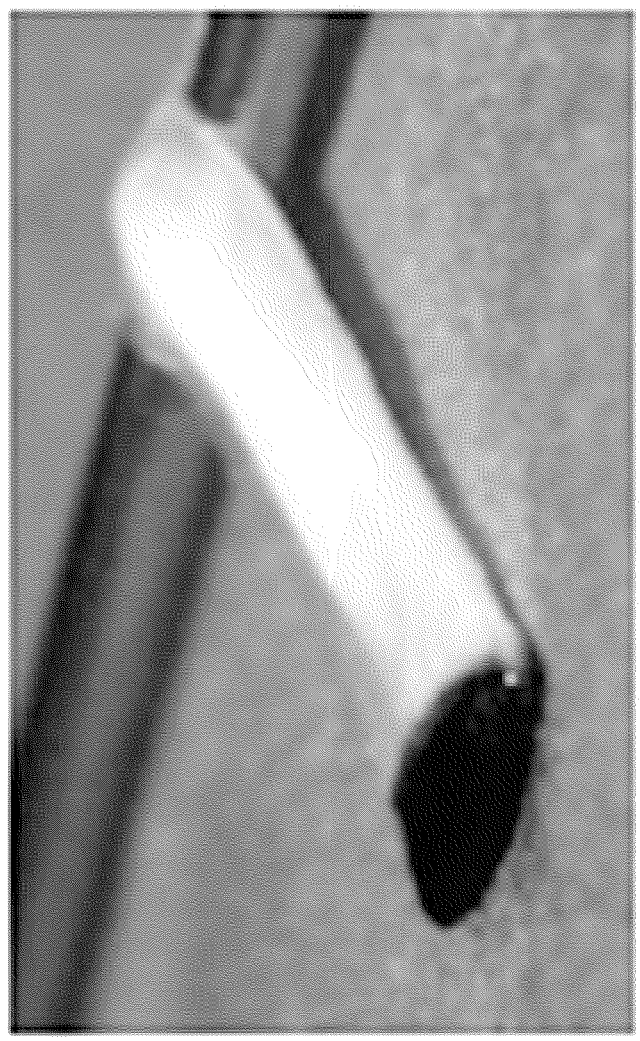
FIG. 10D illustrates the PEFC as being blottable.

The dimensional stability and beneficial properties of the fibrin construct are evidenced by FIGS. 10A-10D, which show that the construct was able to be stretched (FIG. 10A), sutured (FIG. 10B), compressed, trimmed (FIG. 10C) and blotted (FIG. 10D).

Fresh human blood samples were obtained from 6 donors with 15% ACD-A. The 8 ml samples were transferred to borosilicate glass tubes with 180 μl of 1M $CaCl_2$ solution. Soft spins were performed on each blood sample. Formation of the fibrin constructs was highly reproducible. The fibrin plug height was approximately 40-55% of the height of the plasma layer. In addition, the fibrin constructs demonstrated structural stability over time.

Hard Spin Preparation:

Bovine blood samples were collected and transferred to borosilicate tubes, as described above. The samples were then centrifuged at 3000×g for 15 mins. The resulting construct had a fibrin plug layer that was condensed into a thinner layer than obtained in the soft spin preparations. The blood cell layer also separated into a red blood cell layer with a platelet/white blood cell layer below the fibrin plug layer. See FIG. 11.

Fresh human blood samples were obtained from 6 donors with 15% ACD-A. The 8 ml samples were transferred to borosilicate glass tubes with 180 µl of 1M $CaCl_2$ solution. The samples were hard spun at 3000×g for 15 mins. Robust fibrin plugs were obtained in all preparations. Reproducibility was also seen across all the samples. The fibrin plug layer varied in thickness from 2.5 mm to 4.0 mm. In addition, the fibrin constructs demonstrated dimensional and structural stability over time.

Soda-Lime Glass:

To test the reproducibility in glass containers other than borosilicate, soda-lime glass containers were used with the soft spin method. Fresh human blood samples from the same 6 donors described above were collected with 15% ACD-A. The 6.8 ml samples were transferred to borosilicate glass tubes with 180 µl of 1M $CaCl_2$ solution. The samples were centrifuged at 2000×g for 10 mins. After spinning, two of the six samples formed a fibrin plug layer. The other four samples did not form distinct plasma layers or fibrin plug layers. Additionally, two of the four samples also did not exhibit a clear interface between the blood cell layer and the plasma/fibrin layer.

To test if the unclotted samples would eventually form fibrin plugs, two of the four remaining samples were allowed to rest an hour after soft spinning. After one hour, the two samples formed a fibrin plug layer. However, the results indicate that clot formation in soda-lime glass containers does not appear to be reproducible among different samples.

Example 2: Physical Properties of the Platelet Enriched Fibrin Construct

Physical property tests of the fibrin constructs were conducted with constructs prepared with bovine blood collected with ACD-A and shipped the previous day. A total of 18 samples were produced consecutively, with the maximum of 6 samples in centrifuge at a time for 15 minutes at 4500 RPM (2820 g) in capped borosilicate test tubes (with 180 µl of 1M $CaCl_2$ solution). Upon the completion of the spin, the test tubes were immediately removed and placed vertically in holders. The clots, which were ~14 mm in diameter, were extracted one at a time using forceps; excess proximal protein was removed, excess fluid was initially removed with gauze, and then the construct was trimmed to reduce thickness to ~1 mm after a moderate amount of fluids was removed. The constructs were stored in DPBS solution until all samples were prepared and the DPBS fluids were removed from the constructs with light compression with gauze before mechanical testing.

Ultimate Tensile Test:

To test the ultimate failure load of the construct in tension.

A PEFC construct prepared according to the procedure of Example 2 was placed on a gauze pad and lightly covered on both sides to remove a moderate amount of fluids. After 5 minutes in the gauze pad with light compression, the construct was ~14 mm in diameter and ~1 mm in thickness, was further trimmed with parallel cuts on each side to make a 4 mm wide strip. One end of the strip was placed in a stationary clamp The other loose end was placed in another clamp which could be pulled with a force gauge. The clamps were adjusted to remove any slack in the strip between them and a minimal load reading (<0.5N) could be registered on the digital gauge. The force gauge was cleared and set to record peak reading. The construct was pulled very slowly to visualize the failure of the construct through the fibrin layers. Upon failure, record peak load values were noted.

Figure 12:
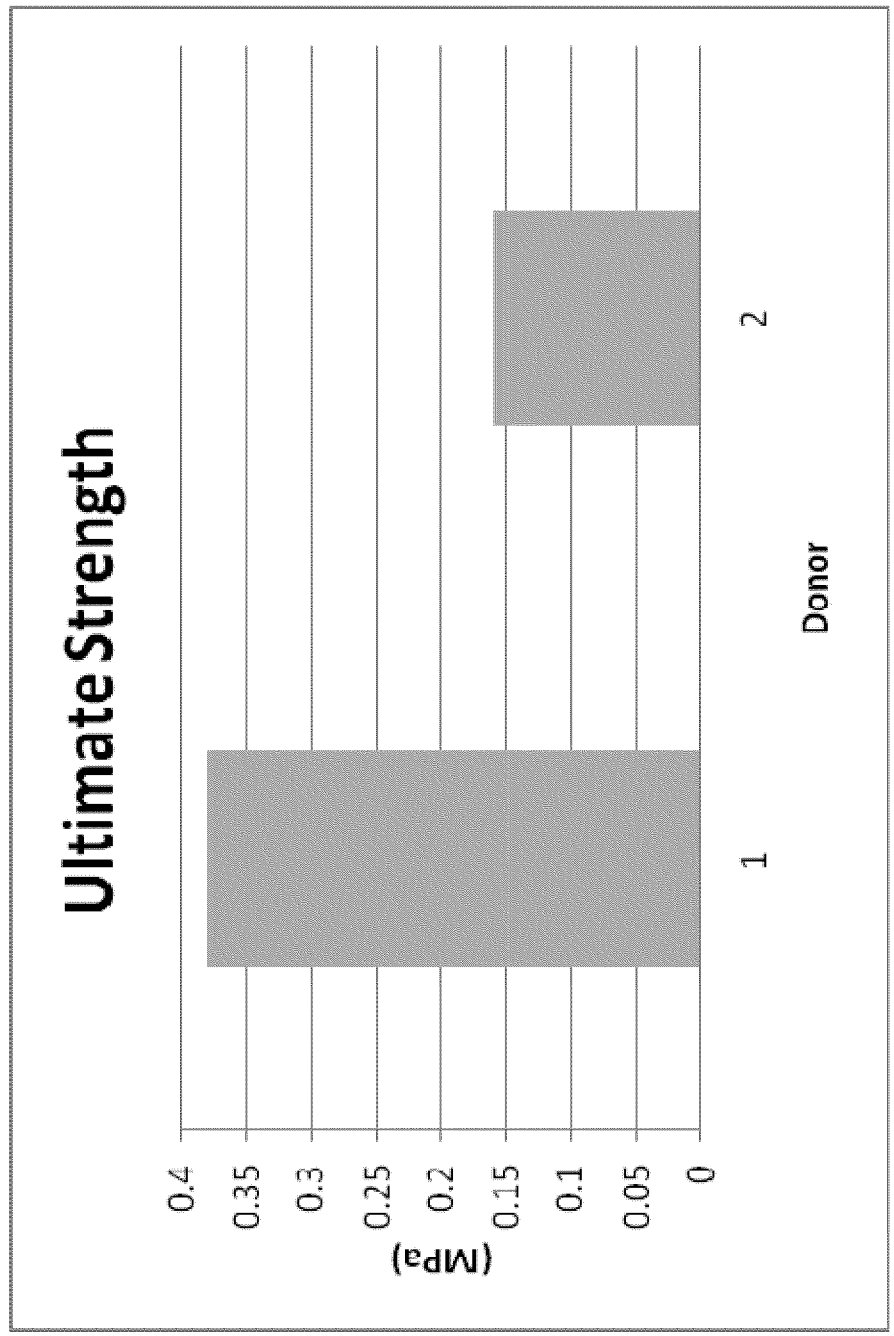
FIG. 12 shows the ultimate strength, or maximum stress exhibited by the constructs.

FIG. 12 shows the ultimate strength, or maximum stress that the constructs withstood prior to failure, that was measured for the constructs obtained from two different donors.

Elongation Tensile Test:

To test the elongation to failure of the construct in tension.

A PEFC construct prepared according to the procedure of Example 2 was placed on a gauze pad and lightly covered on both sides to remove a moderate amount of fluids. After 5 minutes in the gauze pad with light compression, the construct ~14 mm in diameter and ~1 mm in thickness, was further trimmed with parallel cuts on each side to make a 4 wide mm strip. One end of the strip was placed in a stationary clamp. The other loose end was placed in another clamp which could be pulled with a force gauge. The clamps were adjusted to remove any slack in the strip between them and a minimal load reading (<0.5N) could be registered on the digital gauge. The length of the free strip was measured and recorded. Next, the clamp with the force gauge was pulled until the strip ruptured. The distance between the clamps was measured and recorded again. The percent elongation was calculated from this data.

Figure 13:
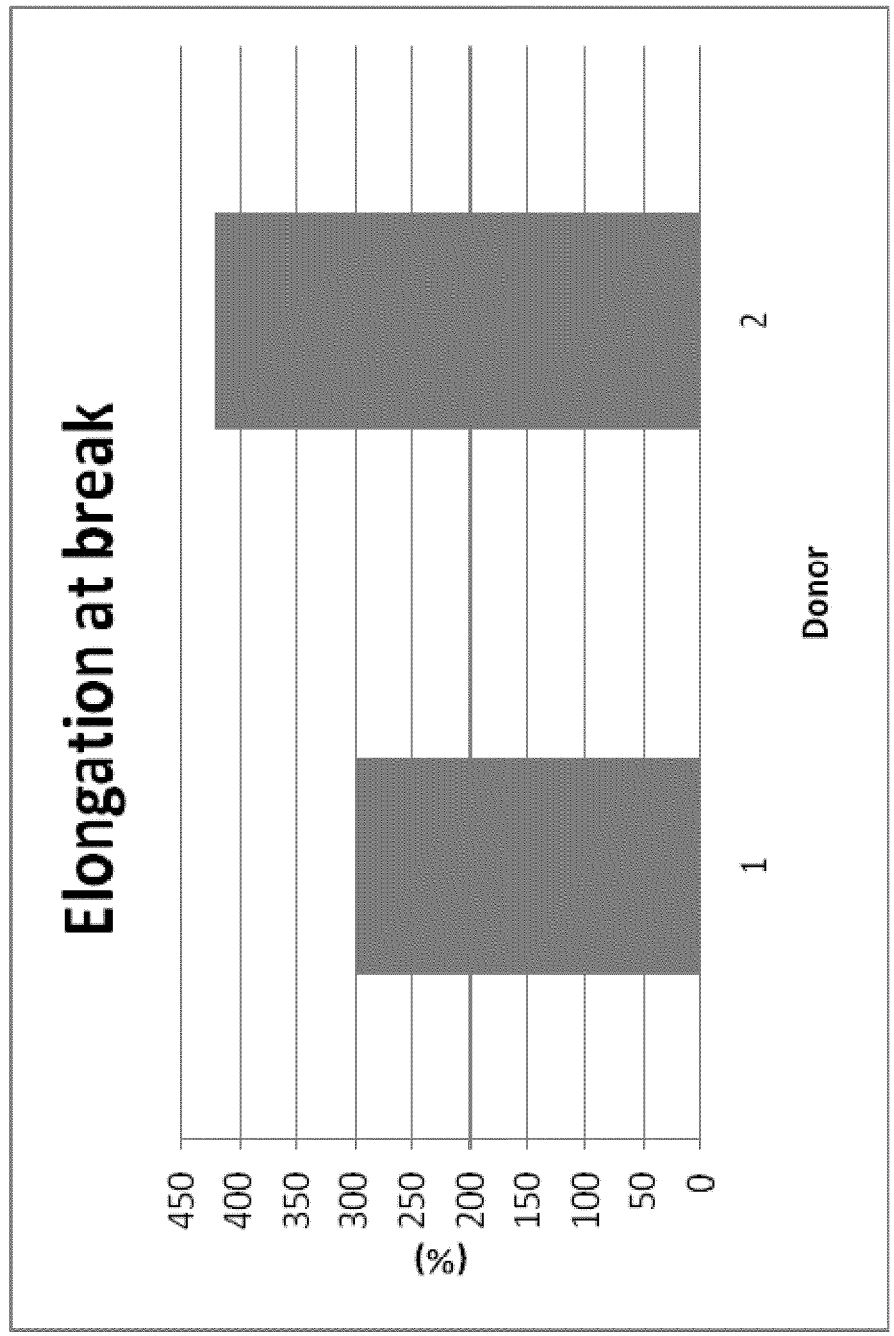
FIG. 13 shows the elongation at break, or the amount of stress exhibited by the constructs prior to failure.

FIG. 13 shows the elongation at break, or the amount of stress that the constructs withstood prior to failure, that was measured for the constructs obtained from two different donors.

Compression Test:

To test the resistive mechanical property of the construct in compression through a displacement half of the construct height.

A PEFC construct prepared according to the procedure of Example 2 was placed on a gauze pad and lightly covered on both sides to remove a moderate amount of fluids. After 5 minutes in the gauze pad with light compression, the construct was ~14 mm in diameter and ~1 mm in thickness. With two solid constructs placed on top of each other, the samples were placed on the plate directly under a force gauge's compression rod, which could be translated using a micrometer. The micrometer was dialed down slowly until a load was registered on the force gauge less than <0.5N. Compared with a micrometer reading taken without the sample in place, the exact thickness of the sample was calculated. The force gauge was cleared and set to record peak reading. The micrometer was dialed down slowly and consistently to compress the sample to half its initial thickness and the peak load was recorded.

Figure 14:
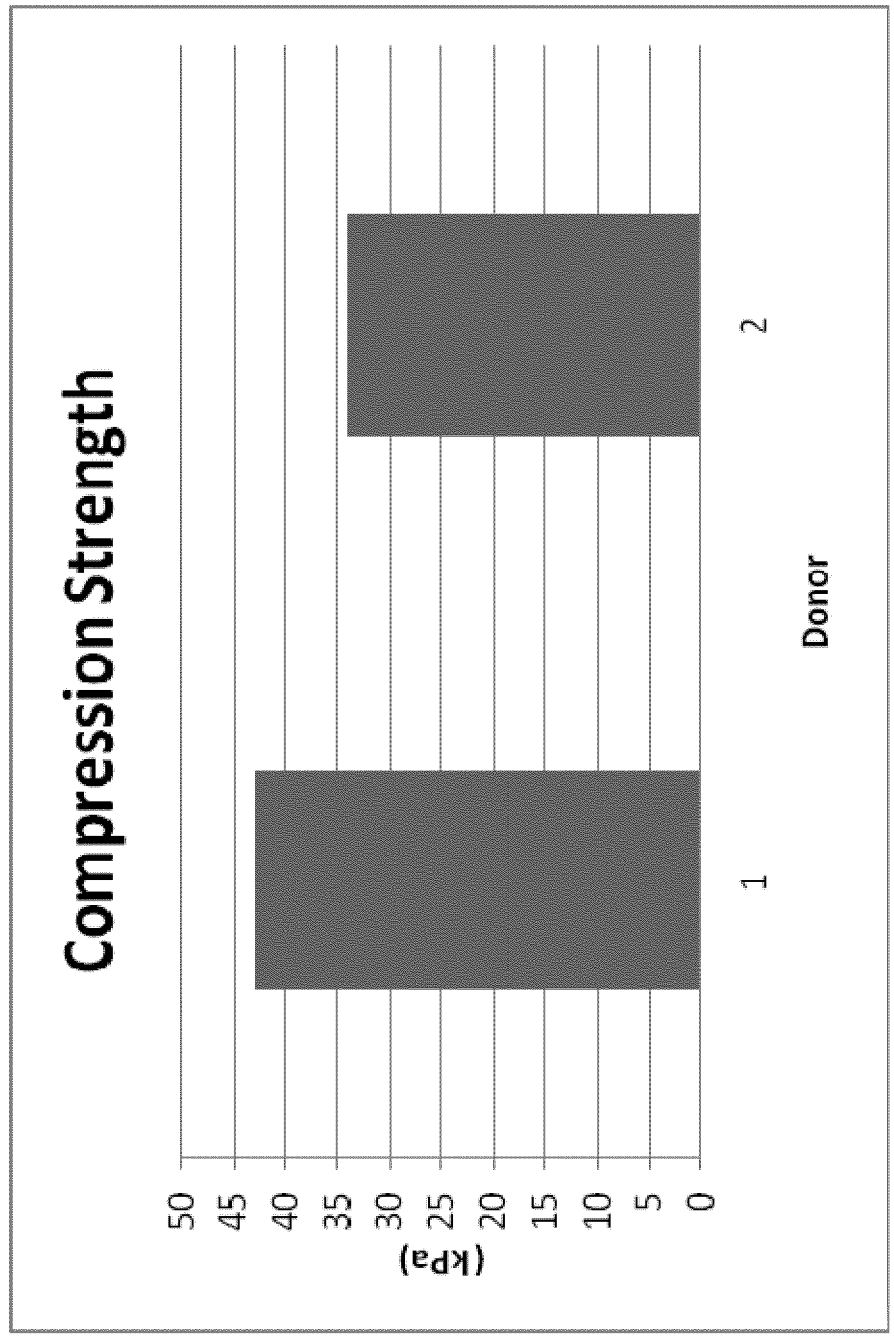
FIG. 14 shows the compression strength, axial forces exhibited by the fibrin constructs prior to being crushed.

FIG. 14 shows the compression strength, axial forces that the fibrin constructs withstood prior to being crushed, that was recorded for two fibrin constructs obtained from two different donors.

Example 3: Biochemical Properties of the Platelet Enriched Fibrin Construct

Histology:

Human PEFC clots were generated according to the procedure of Example 1. Clots were gently blotted on kimwipes to remove excess fluid, cut into 3 sections and mounted in OCT compound on dry ice so that the cut edge created the plane for sectioning. Frozen cassettes were then sectioned in a cryostat ultra microtome at a thickness of approximately 5 microns. Tissues were immediately fixed in 100% methanol for 5 minutes at room temperature after mounting on glass slides. Slides were rinsed in phosphate buffered saline and then subjected to Wright-Giemsa staining following a standard whole blood smear staining protocol. Photomicrographs were obtained from the same field of view at increasing magnifications, as indicated in FIG. 15, using a Zeiss microscope outfitted with a digital color CCD camera.

Figure 15:
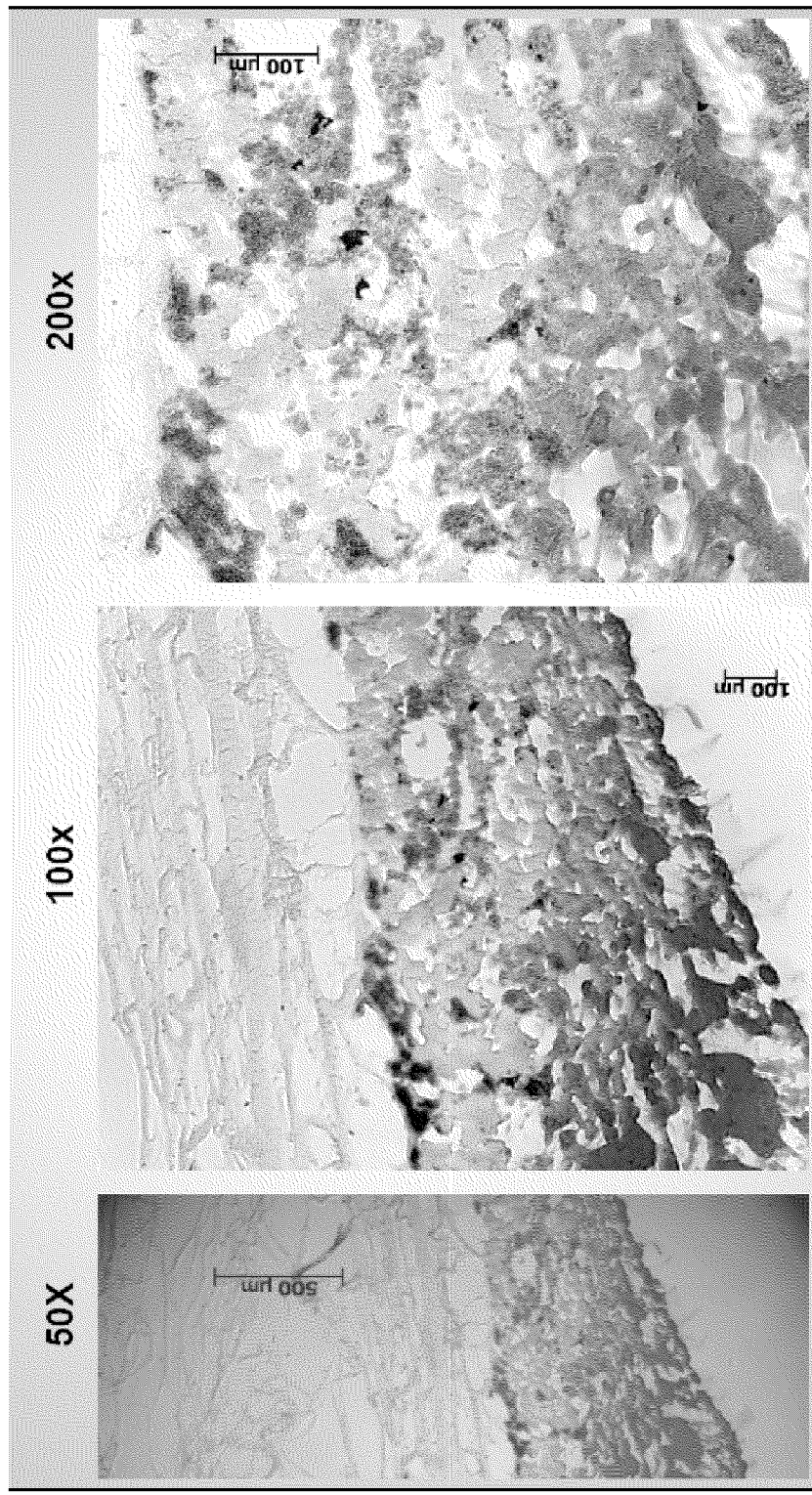
FIG. 15 shows Wright-Giemsa staining of sections of the PEFC at 50×, 100× and 200× magnification.

FIG. 15 shows the stained sections of the PEFC at 50×, 100× and 200×. The upper non-stained portion is the fibrin, the middle section shows the stained platelets and white blood cells and the bottom shows the stained red blood cells.

Figure 16:
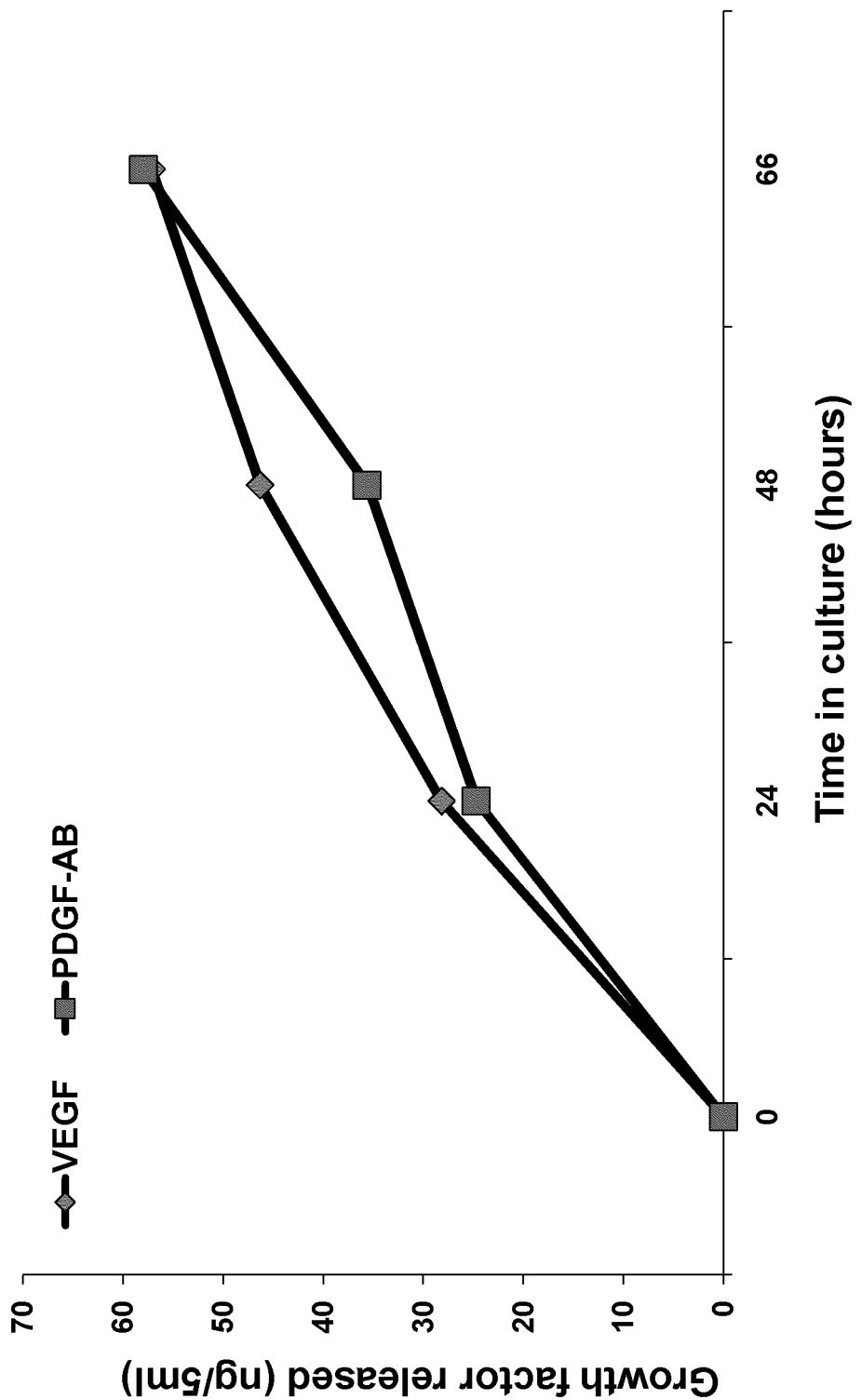
FIG. 16 is a graph showing the VEGF and PDGF-αβ released from the PEFC in 5 ml of medium.

ELISA Assays:

Human PEFC clots were generated according to Example 1. PEFC was placed in a 6-well culture plate well containing 5 ml of serum-free RPMI1640 medium supplemented with penicillin, streptomycin, fungazone, and L-glutamine. At the 0 hr, 24 hrs, 48 hrs and 66 hrs time points, 300 ul of medium from each sample was removed and centrifuged at 3000×g to remove cellular material. 50 ul aliquots of the cleared medium were frozen at −80° C. until the end of the study. All samples were diluted into the linear range of the ELISA assays using the base culture medium described above. ELISA assays for human VEGF and PDGF-AB (BD Biosciences, Sparks Md.) were carried out in triplicate according to the manufacturer's instructions. Data, shown in FIG. 16, represents the total growth factor content in 5 ml of medium.

Figure 17:
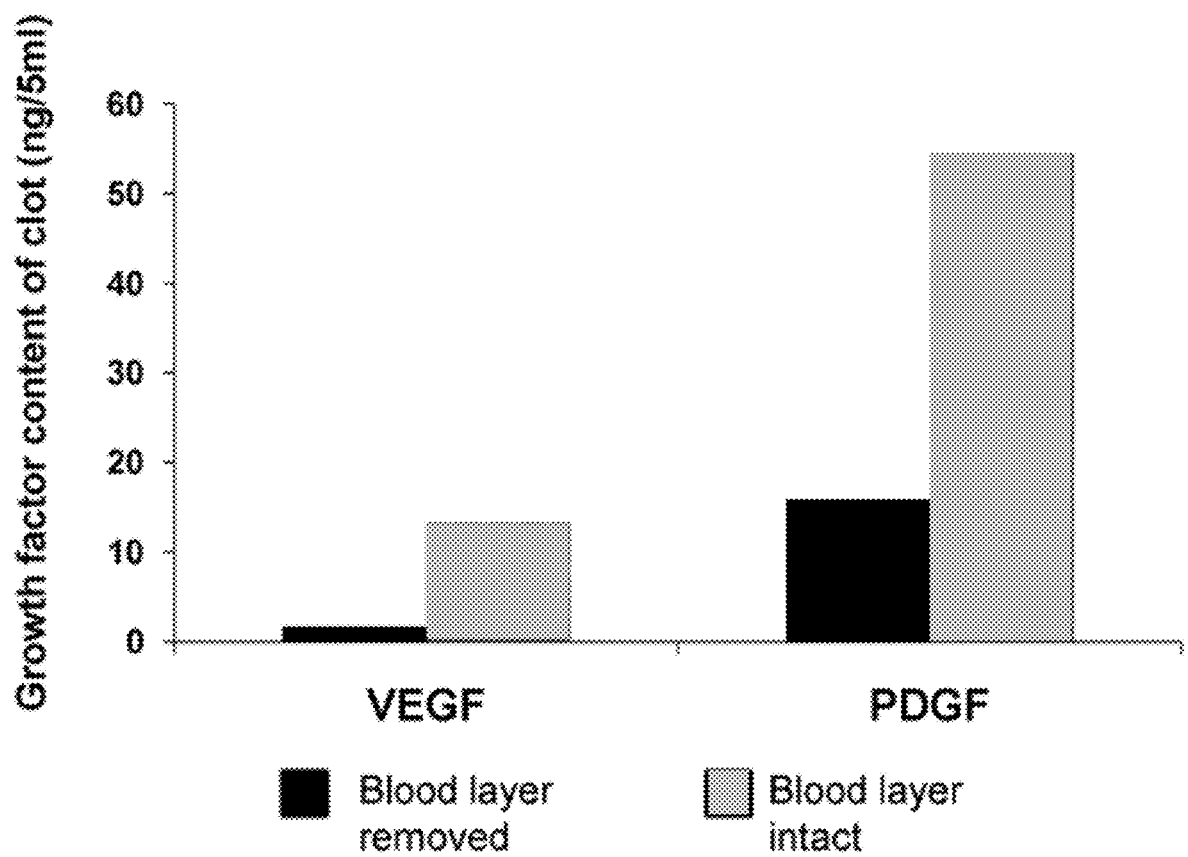
FIG. 17 is a bar graph showing the VEGF and PDGF-αβ content of PEFC with blood cell cap removed or with blood cell cap intact.

Growth Factor Analysis:

Human PEFC were generated as described above and blotted on kimwipes to remove loosely associated red blood cells and excess fluid. One set of clots was subjected to a blunt dissection procedure where the distal red layer comprising the cells/platelets rich region of the clot was removed by peeling it away from the dense fibrin matrix using forceps. Each clot was weighed and then minced into ~2 mm cubes using 2 opposing scalpels, and the pieces were homogenized in PBS supplemented with 0.05% triton X-100 and a protease inhibitor cocktail (Thermo Fisher Scientific, Rockford, Ill.). Homogenates were then diluted into the linear range of the ELISA assays using homogenization buffer. ELISA assays for human VEGF and PDGF-AB (BD Biosciences, Sparks Md.) were carried out in triplicate according to the manufacturer's instructions. Data shown in FIG. 17 represents the total growth factor content of the clot.

Example 4: Delivery of the Platelet Enriched Fibrin Construct

After preparation of the PEFC, nearly 80% of the platelets and growth factors contained in the PEFC are concentrated in a thin layer on one side of the fibrin disk substrate. This layer may not be integrated into the fibrin layer and may be rubbed off upon harsh handling.

Figure 18B:
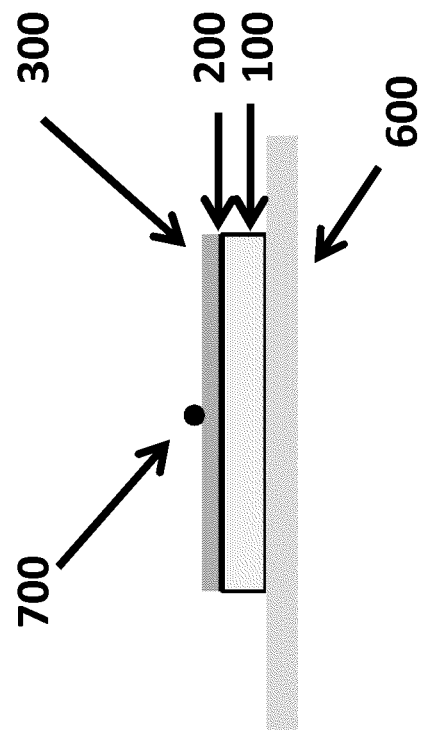
FIG. 18B shows a schematic cross-section of the PEFC with the temporary guiding pin.
Figure 18A:
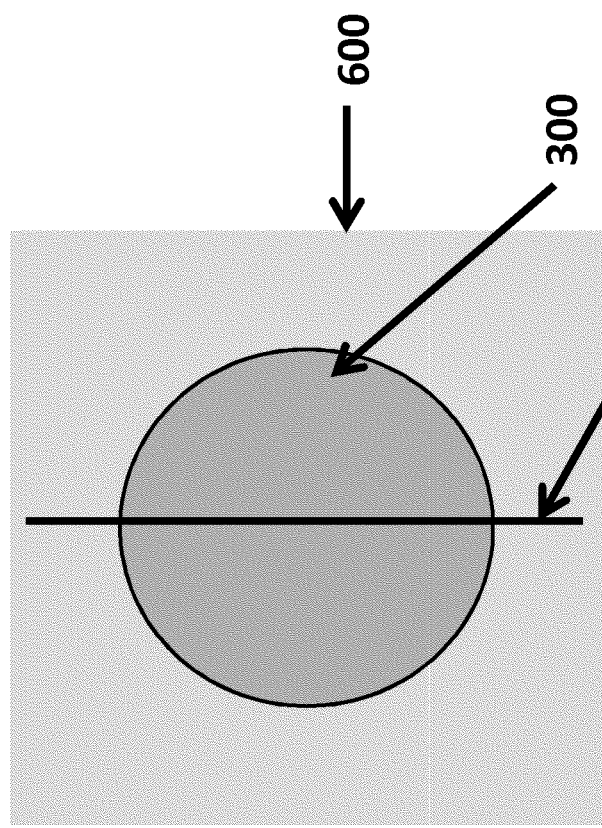
FIG. 18A shows a schematic top view of the PEFC with a temporary guiding pin across the PEFC.
Figure 19B:
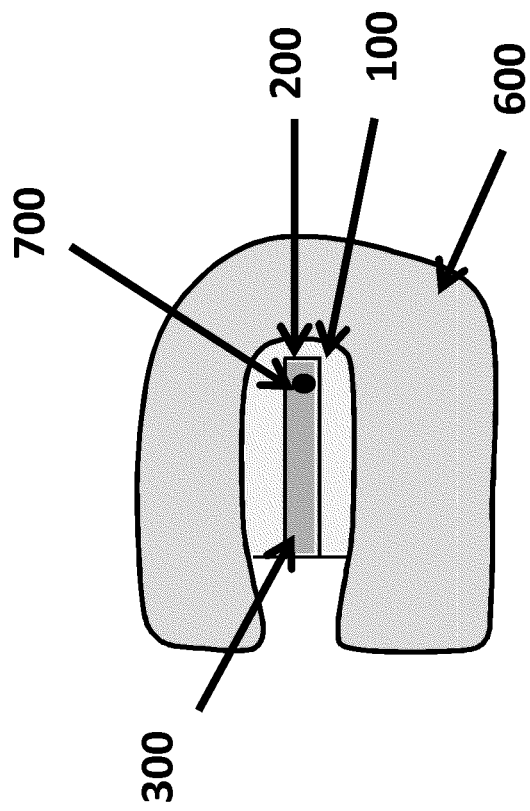
FIG. 19B shows a schematic cross-section of the folded PEFC with the gauze.
Figure 19A:
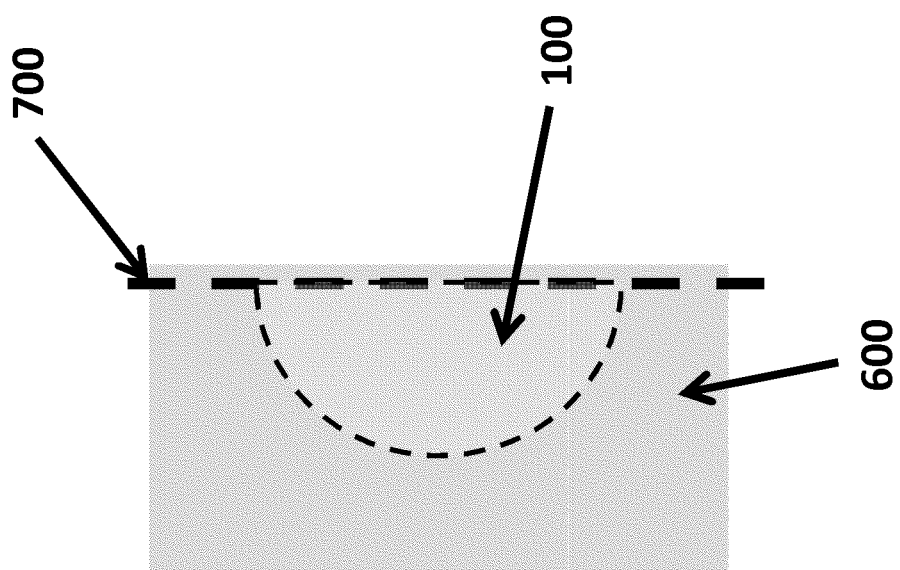
FIG. 19A shows a schematic top view of the PEFC folded with the gauze.
Figures 20A, 20B:
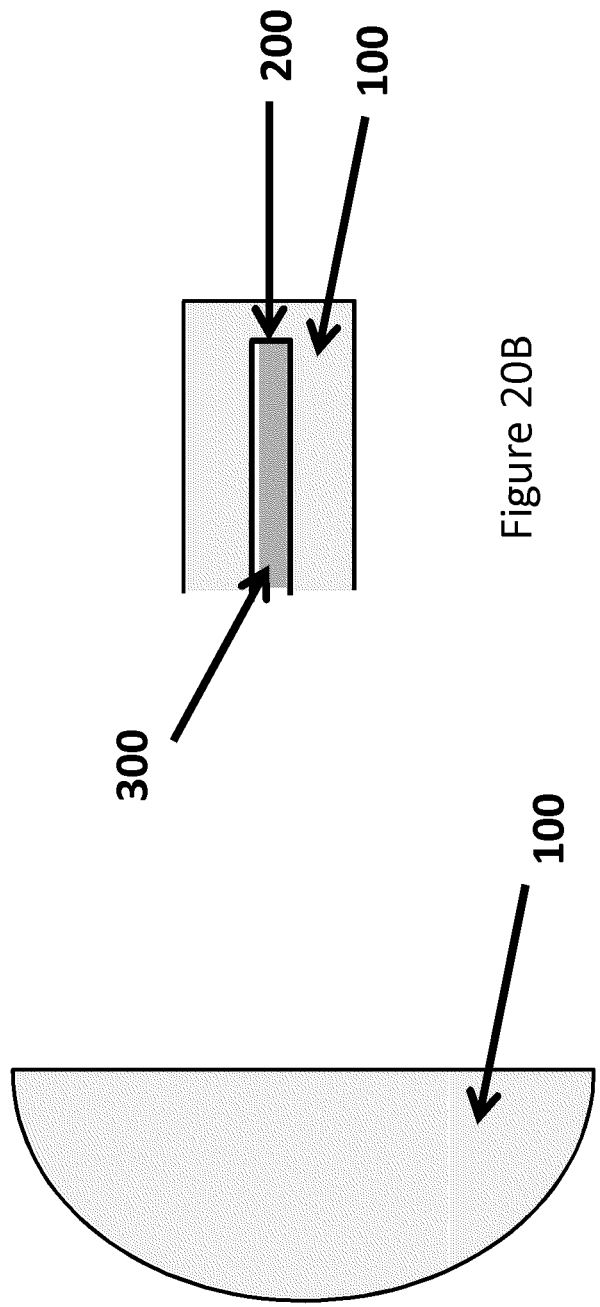
FIG. 20A shows a schematic top view of the folded PEFC removed from the gauze.
FIG. 20B shows a schematic cross-section of the folded PEFC.
Figure 21B:
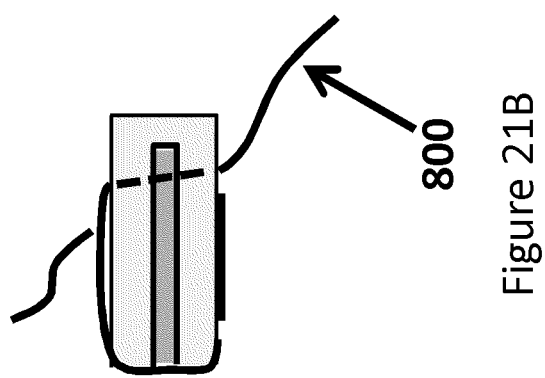
FIG. 21B shows a schematic cross-section of the folded PEFC sutured along the open edge.
Figure 21A:
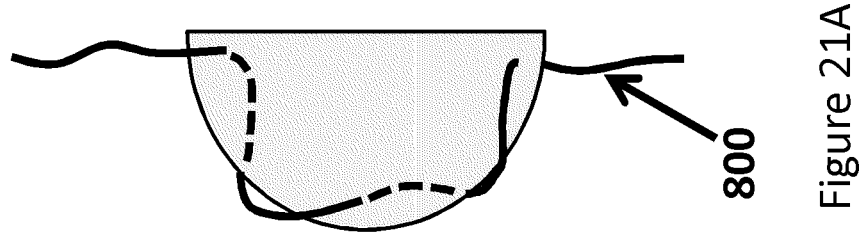
FIG. 21A shows a schematic top view of the folded PEFC sutured along the open edge.

An effective way to protect the platelet/WBC/growth factor rich layer 200 during delivery is to fold the construct in half such that the fibrin layer 100 is on the outside forming a protective jacket, such a folding technique is illustrated in FIG. 6, which shows a cross-section. The RBC layer 300 on the inside provides a tacky surface, so that the folded shape of the PEFC is stable. This can easily be accomplished by first placing the PEFC on a gauze pad, 600, with the RBC layer 300 on top, as shown in FIG. 5A and FIG. 5B, and then placing a temporary guiding pin 700 across the PEFC along the midline (see FIGS. 18A and 18B). The PEFC can then be easily folded together with the gauze pad 600, as shown in FIG. 19A and FIG. 19B. Applying light finger pressure on the gauze lightly adheres the tacky RBC surfaces 300 together. The resulting folded PEFC, shown in FIG. 20A and FIG. 20B, has sufficient mechanical properties and dimensional stability to allow for sutures 800 to be passed therethrough, as demonstrated by FIG. 21A and FIG. 21B.

A number of stitches may be placed separately or a single suture may be used along the edge. The suture tails may optionally be used to aid delivery to the surgical site. Depending on the type of stitch pattern, the suture may be removed after delivery.

Alternatively, an even number of PEFCs may be generated during one centrifugation cycle depending on the capacity of the centrifuge used. Each pair of PEFCs can be placed on top of each other, such that the platelet/WBC/growth factor rich layers 200 are protected by the RBC layers 300 on one side and the fibrin layers 100 on the other side. The pair of PEFCs can then be blotted between gauze pad layers 600 under light pressure, which lightly adheres the tacky surface of the RBC layers 300 together (FIG. 7). Further, the construct can be joined with sutures 800 such as about is perimeter, as shown in FIG. 8, to create a robust construct protecting the contents during delivery.

A desirable and anticipated side benefit of folding or sandwiching the PEFCs is an increase in the time constant of the growth factor release profile due to the added diffusion pathway.

One of skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of reproducibly preparing a growth factor enriched fibrin construct, comprising:
   (a) collecting a human blood sample comprising unaggregated fibrin, wherein collecting the blood sample comprises exposing the blood sample to an anti-coagulant;
   (b) mixing the blood sample in a borosilicate glass container with a coagulation activator consisting of a calcium salt to initiate aggregation of the fibrin;
   (c) exposing the blood mixture to a separation force, thereby producing a dimensionally stable, suturable growth factor enriched fibrin construct comprising a fibrin layer, a platelet layer and a red blood cell layer, wherein said separation force is a single centrifugation with a speed of about 2000 g to about 3,000 g;
   wherein the fibrin construct has a growth factor enriched surface concentrated with blood cells and platelets and an opposed, growth factor depleted surface; wherein the growth factor enriched surface is capable of releasing a growth factor and wherein the released growth factor comprises at least about 5 ng of vascular endothelial growth factor (VEGF) within 24 hours.

2. The method of claim 1, wherein the growth factor depleted surface is substantially lacking in blood cells.

3. The method of claim 1, wherein the growth factor depleted surface is substantially lacking in red blood cells.

4. The method of claim 1, wherein the growth factor depleted surface includes white blood cells.

5. The method of claim 1, wherein the blood cells comprise white blood cells and platelets.

6. The method of claim 1, wherein the step of collecting the blood sample comprises obtaining blood from a single donor.

7. The method of claim 1, wherein the step of collecting the blood sample comprises obtaining blood from multiple donors.

8. The method of claim 1, wherein the anti-coagulant is anticoagulant citrate dextrose solution A and the coagulation activator is calcium chloride.

9. The method of claim 1, further comprising removing excess liquid from the fibrin construct by blotting the fibrin construct on an absorbent material.

10. The method of claim 1, further comprising folding the fibrin construct upon itself to form a folded construct such that adjacent halves of the growth factor enriched surface contact each other and form an inner portion of the folded construct while the growth factor depleted surface forms an outer portion of the folded construct.

11. The method of claim 1, further comprising forming a multilayered construct by layering a second fibrin construct on top of the first fibrin construct such that the growth factor enriched surfaces of each construct are in contact with each other and the growth factor depleted surfaces of each of the constructs form outer surfaces of the multilayered construct.

12. The method of claim 1, further comprising cross-linking the fibrin construct.

13. The method of claim 1, wherein a height of the fibrin plug layer is about 40% to 55% of a height of the plasma layer.

\* \* \* \* \*